(12) United States Patent
Brait et al.

(10) Patent No.: US 11,577,235 B1
(45) Date of Patent: Feb. 14, 2023

(54) LAYERED CATALYST REACTOR SYSTEMS AND PROCESSES FOR HYDROTREATMENT OF HYDROCARBON FEEDSTOCKS

(71) Applicant: Chevron U.S.A. Inc., San Ramon, CA (US)

(72) Inventors: Axel Brait, San Rafael, CA (US);
Xiaoying Ouyang, El Cerrito, CA (US);
Alexander Kuperman, Orinda, CA (US); Theodorus Ludovicus Michael Maesen, San Ramon, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/401,757

(22) Filed: Aug. 13, 2021

(51) Int. Cl.
| | |
|---|---|
| *B01J 21/04* | (2006.01) |
| *B01J 21/06* | (2006.01) |
| *B01J 21/08* | (2006.01) |
| *B01J 21/12* | (2006.01) |
| *B01J 21/16* | (2006.01) |
| *B01J 23/28* | (2006.01) |
| *B01J 23/30* | (2006.01) |
| *B01J 23/42* | (2006.01) |
| *B01J 23/44* | (2006.01) |

(Continued)

(52) U.S. Cl.
CPC .......... *B01J 35/0006* (2013.01); *B01J 21/04* (2013.01); *B01J 21/16* (2013.01); *B01J 23/42* (2013.01); *B01J 23/44* (2013.01); *B01J 23/8885* (2013.01); *B01J 35/10* (2013.01)

(58) Field of Classification Search
CPC .......... B01J 21/04; B01J 21/063; B01J 21/08; B01J 21/12; B01J 21/16; B01J 23/28; B01J 23/30; B01J 23/42; B01J 23/44; B01J 23/6525; B01J 23/6527; B01J 23/75; B01J 23/755; B01J 23/882; B01J 23/883; B01J 23/8885; B01J 23/8913; B01J 83/892; B01J 83/8993; B01J 35/0006; C07C 4/06; C07C 5/02; C07C 6/00

See application file for complete search history.

(56) References Cited

U.S. PATENT DOCUMENTS

| | | | | |
|---|---|---|---|---|
| 3,972,833 A | * | 8/1976 | Michalko | C10G 45/08 502/8 |
| 4,257,918 A | * | 3/1981 | Ginger | B01J 37/04 502/316 |

(Continued)

FOREIGN PATENT DOCUMENTS

| | | |
|---|---|---|
| WO | WO-2018098028 A1 | 5/2018 |
| WO | WO-2022046623 A1 | 3/2022 |

OTHER PUBLICATIONS

ISR and Written Opinion for PCT/US2022/35360, dated Sep. 21, 2022.

*Primary Examiner* — Cam N. Nguyen
(74) *Attorney, Agent, or Firm* — King & Spalding LLP

(57) ABSTRACT

A layered catalyst reactor system and process for hydrotreatment of hydrocarbon feedstocks. The layered catalyst system reactors comprise vertical bed layers including a demetallization catalyst layer, multiple layers of supported hydrotreating catalyst layer, and multiple alternating layers of supported hydrocracking catalysts and self-supported hydrotreating catalysts. The arrangement of the catalyst layers mitigates the risk of temperature run-aways, with improvements in hydrotreatment performance.

21 Claims, 13 Drawing Sheets

(51) Int. Cl.
*B01J 23/75* (2006.01)
*B01J 23/755* (2006.01)
*B01J 23/882* (2006.01)
*B01J 23/883* (2006.01)
*B01J 23/888* (2006.01)
*B01J 23/89* (2006.01)
*B01J 35/00* (2006.01)
*C07C 4/06* (2006.01)
*C07C 5/02* (2006.01)
*C07C 6/00* (2006.01)
*B01J 35/10* (2006.01)

(56) References Cited

U.S. PATENT DOCUMENTS

| | | | | |
|---|---|---|---|---|
| 4,448,896 A | * | 5/1984 | Kageyama | B01J 23/85 502/314 |
| 4,618,594 A | * | 10/1986 | Tait | B01J 35/1042 502/204 |
| 4,900,711 A | * | 2/1990 | Nebesh | B01J 35/1019 502/263 |
| 6,306,289 B1 | * | 10/2001 | Hayashi | B01J 35/10 502/235 |
| 6,551,500 B1 | * | 4/2003 | Ishida | B01J 35/1019 502/313 |
| 7,544,632 B2 | * | 6/2009 | Soled | B01J 37/03 502/220 |
| 7,790,019 B2 | * | 9/2010 | Euzen | B01J 29/74 502/64 |
| 7,816,299 B2 | * | 10/2010 | Schleicher | C10G 49/002 502/313 |
| 7,824,541 B2 | * | 11/2010 | Bhan | B01J 35/1061 502/313 |
| 8,372,772 B2 | * | 2/2013 | Stockwell | B01J 29/084 502/79 |
| 8,530,373 B2 | * | 9/2013 | Bhan | B01J 27/1853 502/313 |
| 2011/0042270 A1 | * | 2/2011 | Guillon | B01J 37/0009 502/67 |
| 2011/0294657 A1 | | 12/2011 | Soled et al. | |
| 2014/0066293 A1 | * | 3/2014 | Han | B01J 27/0515 502/220 |
| 2014/0066294 A1 | * | 3/2014 | Han | C10G 45/08 502/220 |
| 2014/0135207 A1 | * | 5/2014 | Han | B01J 27/0515 502/220 |
| 2015/0136646 A1 | | 5/2015 | Zhan et al. | |

\* cited by examiner

LAYERED CATALYST REACTOR SYSTEMS AND PROCESSES FOR HYDROTREATMENT OF HYDROCARBON FEEDSTOCKS

TECHNICAL FIELD

The present disclosure relates to layered catalyst reactor systems and processes for use in hydrocarbon reforming.

BACKGROUND

Catalytic hydroprocessing refers to petroleum refining processes in which a carbonaceous feedstock is brought into contact with hydrogen and a catalyst, at a higher temperature and pressure, for the purpose of removing undesirable impurities and/or converting the feedstock to an improved product. Examples of hydroprocessing processes include hydrotreating, hydrodemetallization, hydrocracking and hydroisomerization processes.

Hydrotreating processes are used to remove impurities, such as sulfur, nitrogen and oxygen for the control of a final product specification or for the preparation of feed for further processing. Supported mixed metal catalysts used for hydrotreatment of carbonaceous feedstocks comprise a porous alumina matrix impregnated with combinations of nickel, molybdenum, tungsten and/or cobalt. Self-supported mixed metal sulfide catalysts, which are not diluted by a support, pack more metal sulfide and therefore, more hydrogenation power into a smaller reactor volume as compared to supported mixed metal sulfide catalysts.

However, self-supported catalysts are more susceptible to localized "run-away" temperature increases than supported catalysts. Such run-away temperature increases occur when a hydrogenation catalyst generates more heat than its surroundings can absorb, becoming hotter than the bed or reactor temperature. The resulting temperature increase accelerates the hydrogen consumption, which further increases the catalyst temperature until the hydrogenation (hydrogen consumption) rate exceeds the hydrogen supply rate. At that stage the catalyst starts to dehydrogenate the feed, generating coke and hydrogen. This process leads to irreversible coke deactivation.

Supported hydroprocessing catalysts typically comprise one or more metals deposited on a support or carrier consisting of an amorphous oxide and/or a crystalline microporous material (e.g., a zeolite). A suitably sized top layer of supported hydrotreating catalysts can be used to protect a bottom layer of self-supported catalysts from excessive hydrogenation activity.

In view of the foregoing, there is an ongoing need to provide improved hydrotreating catalyst systems that minimize the risk of run-away temperature increases, while increasing the activity and efficiency of the hydrotreatment process.

SUMMARY

This summary is provided to introduce various concepts in a simplified form that are further described below in the detailed description. This summary is not intended to identify required or essential features of the claimed subject matter nor is the summary intended to limit the scope of the claimed subject matter.

Aspects of the disclosure are directed to layered catalyst reactor systems and processes for hydrotreatment of hydrocarbon feedstocks.

In one aspect, a layered catalyst reactor system comprises a vertical bed or stack of catalyst layers arranged from top to bottom in the following order:

(i) a layer comprising one or more demetallization catalysts, which is about 5 to about 25% of the total volume of catalysts in the vertical bed;

(ii) a layer of one or more supported hydrotreating catalysts, which is about 17 to about 27% of the total volume of catalysts in the vertical bed;

(iii) a layer of one or more supported hydrocracking catalysts, which is about 5 to about 15% of the total volume of catalysts in the vertical bed;

(iv) a layer of one or more self-supported hydrotreating catalysts, which is about 5 to about 25% of the total volume of catalysts in the vertical bed;

(v) a layer of one or more supported hydrocracking catalysts, which is about 5 to about 15% of the total volume of catalysts in the vertical bed;

(vi) a layer of one or more self-supported hydrotreating catalysts, which is about 5 to about 25% of the total volume of catalysts in the vertical bed;

(vii) a layer of one or more supported hydrotreating catalysts, which is about 2 to about 9% of the total volume of catalysts in the vertical bed.

In another aspect, a layered catalyst reactor system comprises a vertical bed or stack of catalyst layers arranged from top to bottom in the following order:

(i) a layer comprising one or more demetallization catalysts, which is about 5 to about 25% of the total volume of catalysts in the vertical bed;

(ii) a layer of one or more supported hydrotreating catalysts, which is about 17 to about 27% of the total volume of catalysts in the vertical bed;

(iii) a layer of one or more supported hydrocracking catalysts, which is about 5 to about 10% of the total volume of catalysts in the vertical bed;

(iv) a layer of one or more self-supported hydrotreating catalysts, which is about 3 to about 15% of the total volume of catalysts in the vertical bed;

(v) a layer of one or more supported hydrocracking catalysts, which is about 5 to about 10% of the total volume of catalysts in the vertical bed;

(vi) a layer of one or more self-supported hydrotreating catalysts, which is about 3 to about 15% of the total volume of catalysts in the vertical bed;

(vii) a layer of one or more supported hydrocracking catalysts, which is about 5 to about 10% of the total volume of catalysts in the vertical bed;

(vii) a layer of one or more supported hydrotreating catalysts, which is about 3 to about 15% of the total volume of catalysts in the vertical bed;

(viii) a layer of one or more supported hydrotreating catalysts, which is about 2 to about 9% of the total volume of catalysts in the vertical bed.

In another aspect, a layered catalyst reactor system comprises a vertical bed or stack of catalyst layers arranged from top to bottom in the following order:

(i) a layer comprising one or more demetallization catalysts:

(ii) a layer of one or more supported hydrotreating catalysts;

(iii) a layer of one or more supported hydrocracking catalysts;

(iv) a layer of one or more self-supported hydrotreating catalysts;

(v) a layer of one or more supported hydrocracking catalysts;

(vi) a layer of one or more self-supported hydrotreating catalysts;

(vii) a layer of one or more supported hydrotreating catalysts;

wherein the of the total volume of the two layers comprising one or more self-supported hydrotreating catalysts is about 10 to about 50% of the of the total volume of catalysts in the vertical bed; and wherein the of the total volume of the two layers comprising one or more supported hydrocracking catalysts is about 10 to about 30% of the of the total volume of catalysts in the vertical bed.

In another aspect, a layered catalyst reactor system comprises a vertical bed or stack of catalyst layers arranged from top to bottom in the following order:

(i) a layer comprising one or more demetallization catalysts:

(ii) a layer of one or more supported hydrotreating catalysts;

(iii) a layer of one or more supported hydrocracking catalysts;

(iv) a layer of one or more self-supported hydrotreating catalysts;

(v) a layer of one or more supported hydrocracking catalysts;

(vi) a layer of one or more self-supported hydrotreating catalysts;

(vii) a layer of one or more supported hydrocracking catalysts;

(viii) a layer of one or more self-supported hydrotreating catalysts;

(ix) a layer of one or more supported hydrotreating catalysts;

wherein the of the total volume of the three layers comprising one or more self-supported hydrotreating catalysts is about 9 to about 45% of the of the total volume of catalysts in the vertical bed; and wherein the of the total volume of the three layers comprising one or more supported hydrocracking catalysts is about 15 to about 30% of the of the total volume of catalysts in the vertical bed.

In another aspect, the present invention is directed to a process for hydrotreatment of hydrocarbon feedstocks comprising: (i) contacting a hydrocarbon feedstock which contains contaminants comprised of metals, sulfur, nitrogen and olefins with a layered catalyst reactor system as described herein in the presence of hydrogen to produce hydrocarbon product having a lower content of metals, sulfur, nitrogen and olefins than the hydrocarbon feedstock; (ii) passing the hydrocarbon feedstock sequentially through the layers of the layered catalyst reactor system vertically from top to bottom; and (iii) recovering the hydrocarbon product from the bottom of the layered catalyst reactor system.

This summary and the following detailed description provide examples and are explanatory only of the disclosure. Accordingly, the foregoing summary and the following detailed description should not be considered to be restrictive. Additional features or variations thereof can be provided in addition to those set forth herein, such as for example, various feature combinations and sub-combinations of those described in the detailed description.

DEFINITIONS

Figure 1:
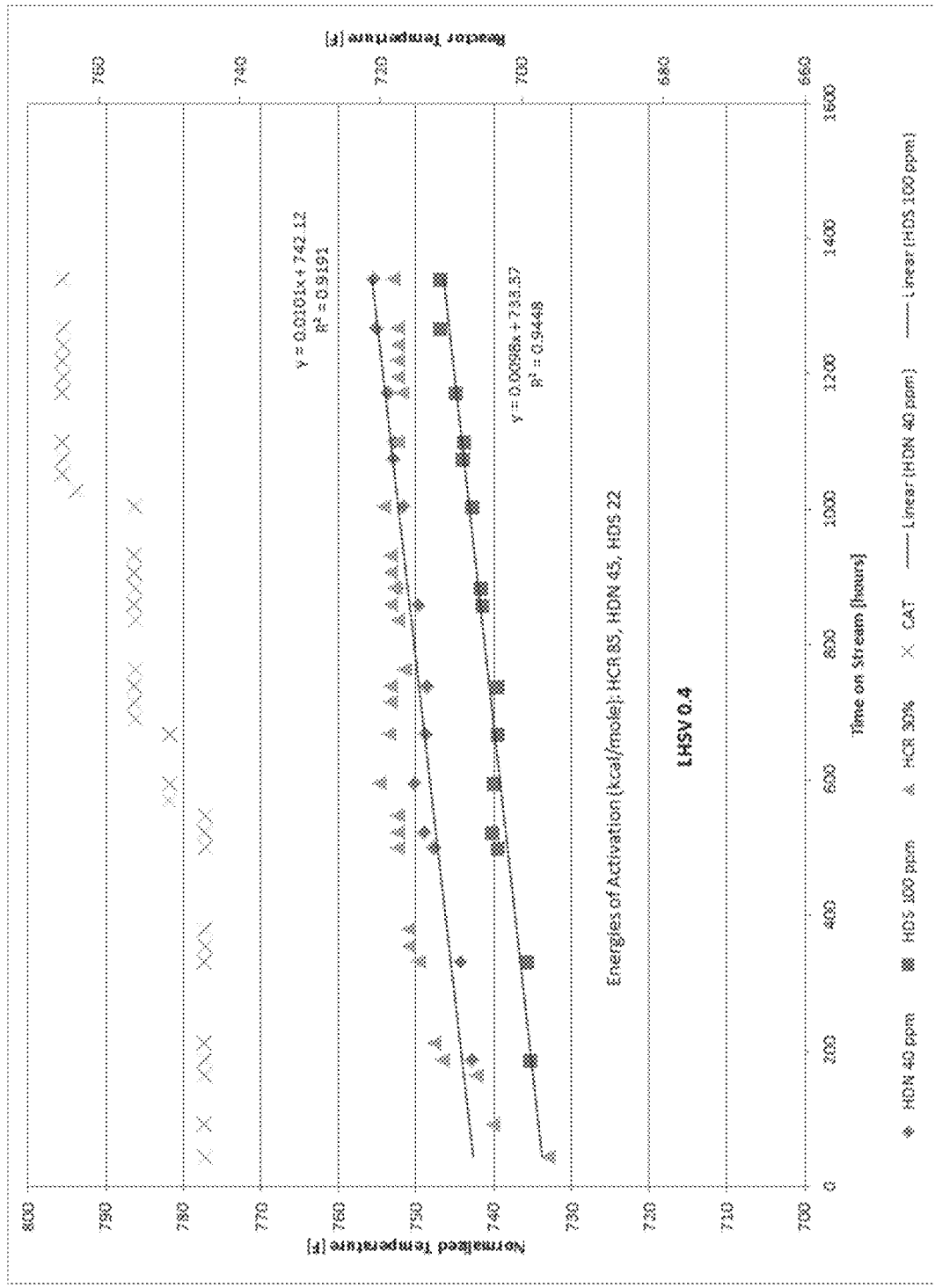
FIG. 1 graphically depicts normalized temperatures for hydrotreatment processes with a comparative layered catalyst reactor system (no hydrocracking or self-supported hydrotreating catalyst layers; BSU 607-56).
Figure 2:
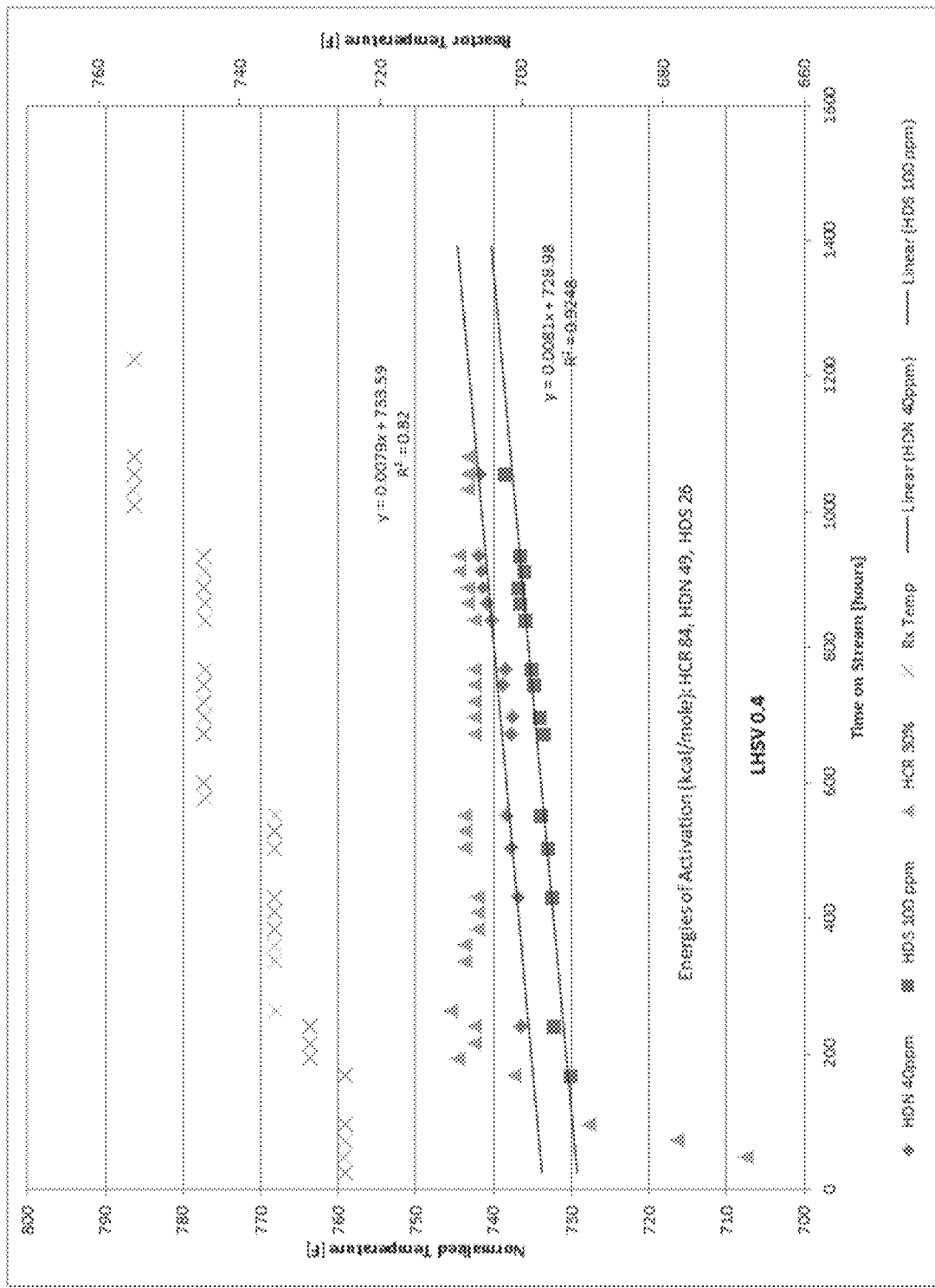
FIG. 2 graphically depicts normalized temperatures for hydrotreatment processes with a comparative layered catalyst reactor system (one hydrocracking catalyst layer and one self-supported hydrotreating catalyst layer; BSU607-57).

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology can be applied, as long as that definition does not conflict with any other disclosure or definition applied herein or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. The terms "including", "with", and "having", as used herein, are defined as comprising (i.e., open language), unless specified otherwise.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, all numerical end points of ranges disclosed herein are approximate, unless excluded by proviso.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±20% of the stated value, ±15% of the stated value, ±10% of the stated value, ±5% of the stated value, ±3% of the stated value, or ±1% of the stated value.

"Periodic Table" refers to the version of IUPAC Periodic Table of the Elements dated Jun. 22, 2007, and the numbering scheme for the Periodic Table Groups is as described in Chemical and Engineering News, 63(5), 27 (1985).

"Hydrocarbonaceous" and "hydrocarbon" refer to a compound containing only carbon and hydrogen atoms. Other identifiers may be used to indicate the presence of particular groups, if any, in the hydrocarbon (e.g., halogenated hydrocarbon indicates the presence of one or more halogen atoms replacing an equivalent number of hydrogen atoms in the hydrocarbon).

"Hydroprocessing" or "hydroconversion" refers to a process in which a carbonaceous feedstock is brought into contact with hydrogen and a catalyst, at a higher temperature and pressure, for the purpose of removing undesirable impurities and/or converting the feedstock to a desired product. Such processes include, but are not limited to, methanation, water gas shift reactions, hydrogenation, hydrotreating, hydrodesulphurization, hydrodenitrogenation, hydrodemetallation, hydrodearomatization, hydroisomerization, hydrodewaxing and hydrocracking including selective hydrocracking. Depending on the type of hydroprocessing and the reaction conditions, the products of hydroprocessing can show improved physical properties such as improved viscosities, viscosity indices, saturates content, low temperature properties, volatilities and depolarization.

"Hydrotreating" refers to a hydrogenation process used to remove contaminants, such as nitrogen, sulfur, oxygen, and metals, from liquid petroleum fractions. In certain embodiments, the hydrotreating process removes at least about 90% of the nitrogen-, sulfur-, oxygen-, and/or metal-containing contaminants. In certain embodiments, hydrotreating processes converts olefins and aromatics to saturated compounds.

"Hydrocracking" refers to a process in which hydrogenation and dehydrogenation accompanies the cracking/fragmentation of hydrocarbons, e.g., converting heavier hydrocarbons into lighter hydrocarbons.

The term "supported", with respect to catalysts (e.g., active phase materials), refers to catalysts which are affixed to conventional materials that are typically a solid with a high surface area. Support materials may be inert or participate in the catalytic reactions. Support materials may be porous or non-porous. Typical catalyst supports include various kinds of carbon, alumina, silica, and silica-alumina, e.g., amorphous silica aluminates, zeolites, alumina-boria, silica-alumina-magnesia, silica-alumina-titania and materials obtained by adding other zeolites and other complex oxides thereto.

The term "self-supported", with respect to catalysts, refers to unsupported catalysts or catalysts which are not affixed to other materials.

The terms "catalyst particles", "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any members of a claimed group.

Although any processes and materials similar or equivalent to those described herein can be used in the practice or testing of the invention, the typical processes and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION

It is to be understood that the disclosure is not limited in its application to the details of construction and the arrangement of components set forth in the following description or illustrated in the drawings.

The present disclosure generally relates to layered catalyst reactor systems and processes for hydroconversion of hydrocarbon feedstocks. The layered catalyst reactor system disclosed herein comprises a configuration of alternating separate layers of supported catalysts and self-supported catalysts which increases the activity and effectiveness of hydrotreatment without increasing the volume of catalysts. In particular, the layered catalyst reactor systems and processes achieve non-monotonic hydrogenation activity through the layering of supported hydrotreating and hydrocracking catalysts in between layers of self-supported hydrotreating catalyst layers, which are highly active. In certain embodiments, the self-supported hydrotreating catalysts are mixed metal sulfide catalysts. The configuration of the catalyst layers in the reactor as disclosed herein can be used to mitigate the risk.

The exemplary layered catalyst reactor systems, wherein two or more self-supported (or unsupported) hydrotreating catalyst layers are sandwiched in between supported catalyst layers outperforms comparable systems in which the supported catalyst layer is on top of a single self-supported catalyst layer with the same of the total volumes of supported and of self-supported catalysts.

The layered catalyst reactor systems are useful for the hydroconversion of hydrocarbon feedstocks or to processes for upgrading petroleum feedstocks. The processes disclosed herein may be used for reacting hydrocarbon feedstocks at conditions of elevated temperatures and pressures in the presence of hydrogen and the layered catalyst reactor systems to convert the feedstock to lower molecular weight products with reduced contaminant levels. The hydroconversion processes are those used for hydrotreating or hydrocracking of a hydrocarbon feedstock, and may include, for example, hydrogenation, desulfurization, denitrogenation, and removal of metals. In one embodiment, the hydroconversion process comprises hydrocracking and/or hydrotreating of hydrocarbon feedstocks.

Layered Catalyst Reactor Systems

In one aspect, the present invention is directed to a layered catalyst reactor system for hydrotreating hydrocarbon feedstock which contains contaminants comprised of metals, sulfur, nitrogen and olefins. The layered catalyst reactor systems can be used to remove impurities, such as metals, sulfur and nitrogen, and to saturate olefins and aromatic compounds.

According to the embodiments, a layered catalyst reactor system comprises a vertical bed or stack of catalyst layers arranged from top to bottom in the following order:

(i) a layer comprising one or more demetallization catalysts, which is about 5 to about 25% of the total volume of catalysts in the vertical bed;

(ii) a layer of one or more supported hydrotreating catalysts, which is about 17 to about 27% of the total volume of catalysts in the vertical bed;

(iii) a layer of one or more supported hydrocracking catalysts, which is about 5 to about 15% of the total volume of catalysts in the vertical bed;

(iv) a layer of one or more self-supported hydrotreating catalysts, which is about 5 to about 25% of the total volume of catalysts in the vertical bed;

(v) a layer of one or more supported hydrocracking catalysts, which is about 5 to about 15% of the total volume of catalysts in the vertical bed;

(vi) a layer of one or more self-supported hydrotreating catalysts, which is about 5 to about 25% of the total volume of catalysts in the vertical bed;

(vii) a layer of one or more supported hydrotreating catalysts, which is about 2 to about 9% of the total volume of catalysts in the vertical bed.

As referred to herein, the "total volume of catalysts in the vertical bed" means the total volume of the materials that form the layers of self-supported and supported catalysts in the vertical bed.

In certain embodiments, one or more of the layers of the one or more self-supported hydrotreating catalysts, is about 9 to about 19%, or about 15 to about 25%, of the total volume of catalysts in the vertical bed. In certain embodiments, layer (iv) is about 9 to about 19% of the total volume of catalysts in the vertical bed. In certain embodiments, layer (vi) is about 15 to about 25% of the total volume of catalysts in the vertical bed.

In certain embodiments, a layered catalyst reactor system comprises a vertical bed or stack of catalyst layers arranged from top to bottom in the following order:

(i) a layer comprising one or more demetallization catalysts, which is about 5 to about 25% of the total volume of catalysts in the vertical bed;

(ii) a layer of one or more supported hydrotreating catalysts, which is about 17 to about 27% of the total volume of catalysts in the vertical bed;

(iii) a layer of one or more supported hydrocracking catalysts, which is about 5 to about 10% of the total volume of catalysts in the vertical bed;

(iv) a layer of one or more self-supported hydrotreating catalysts, which is about 3 to about 15% of the total volume of catalysts in the vertical bed;

(v) a layer of one or more supported hydrocracking catalysts, which is about 5 to about 10% of the total volume of catalysts in the vertical bed;

(vi) a layer of one or more self-supported hydrotreating catalysts, which is about 3 to about 15% of the total volume of catalysts in the vertical bed;

(vii) a layer of one or more supported hydrocracking catalysts, which is about 5 to about 10% of the total volume of catalysts in the vertical bed;

(vii) a layer of one or more self-supported hydrotreating catalysts, which is about 3 to about 15% of the total volume of catalysts in the vertical bed;

(viii) a layer of one or more supported hydrotreating catalysts, which is about 2 to about 9% of the total volume of catalysts in the vertical bed.

In certain embodiments, one or more layers of the one or more self-supported hydrotreating catalysts, is about 4 to about 10%, or about 10 to about 15%, of the total volume of catalysts in the vertical bed. In certain embodiments, layer (iv) is about 4 to about 10% of the total volume of catalysts in the vertical bed. In certain embodiments, layer (vi) is about 10 to about 15% of the total volume of catalysts in the vertical bed. In certain embodiments, layer (viii) is about 10 to about 15% of the total volume of catalysts in the vertical bed.

In certain embodiments, the layered catalyst reactor system comprises a vertical bed or stack of catalyst layers arranged from top to bottom in the following order:

(i) a layer comprising one or more demetallization catalysts:

(ii) a layer of one or more supported hydrotreating catalysts;

(iii) a layer of one or more supported hydrocracking catalysts;

(iv) a layer of one or more self-supported hydrotreating catalysts;

(v) a layer of one or more supported hydrocracking catalysts;

(vi) a layer of one or more self-supported hydrotreating catalysts;

(vii) a layer of one or more supported hydrotreating catalysts;

wherein the total volume of the two layers comprising one or more self-supported hydrotreating catalysts is about 10 to about 50% of the total volume of catalysts in the vertical bed; and wherein the total volume of the two layers comprising one or more supported hydrocracking catalysts is about 10 to about 30% of the total volume of catalysts in the vertical bed.

In certain embodiments, the layered catalyst reactor system comprises a vertical bed or stack of catalyst layers arranged from top to bottom in the following order:

(i) a layer comprising one or more demetallization catalysts:

(ii) a layer of one or more supported hydrotreating catalysts;

(iii) a layer of one or more supported hydrocracking catalysts;

(iv) a layer of one or more self-supported hydrotreating catalysts;

(v) a layer of one or more supported hydrocracking catalysts;

(vi) a layer of one or more self-supported hydrotreating catalysts;

(vii) a layer of one or more supported hydrocracking catalysts;

(viii) a layer of one or more self-supported hydrotreating catalysts;

(ix) a layer of one or more supported hydrotreating catalysts;

wherein the total volume of the three layers comprising one or more self-supported hydrotreating catalysts is about 9 to about 45% of the total volume of catalysts in the vertical bed; and wherein the total volume of the three layers comprising one or more supported hydrocracking catalysts is about 15 to about 30% of the total volume of catalysts in the vertical bed.

In certain embodiments, the total volume of the layer comprising one or more demetallization catalysts is about 5 to about 25% of the total volume of catalysts in the vertical bed. In certain embodiments, the top layer comprises or consists of one or more demetallization catalysts.

In certain embodiments, the total volume of the layers comprising one or more supported hydrotreating catalysts is about 19 to about 36% of the total volume of catalysts in the vertical bed. In certain embodiments, the bottom layer comprises or consists of one or more supported hydrotreating catalysts. In certain embodiments, the layer below and in contact with the top layer comprises or consists of one or more supported hydrotreating catalysts.

In certain embodiments, the total volume of catalyst in the vertical bed is in the range of about 50,000 to about 300,000 ft$^3$. In certain embodiments, the vertical bed has a volume of about 50,000 to about 300,000 ft$^3$.

The exemplary layered catalyst reactor systems comprise multiple zones. The first zone, at the top of the vertical bed, is a demetallization zone, which occurs in the layer comprising one or more demetallization catalysts. The demetallization zone generally involves removing contaminant metals from the hydrocarbon feedstock.

The second zone, below the first zone, is a hydrotreating zone, which occurs in the layer comprising one or more supported hydrotreating catalysts. This hydrotreating zone is designed to selectively minimize inhibitors, such as organic N, organic S and aromatics through hydrogenation, or saturation. This zone helps to protect the subsequent hydrocracking and hydrotreating (e.g., the hydrotreatment with self-supported catalysts) zones, which can be sensitive to the inhibitors.

The third, fourth, fifth and sixth zones are alternating layers of hydrocracking zones followed by hydrotreating zones, wherein the hydrotreatment occurs in the layers comprising one or more self-supported hydrotreating catalysts. In certain embodiments, the one or more self-supported hydrotreating catalysts are mixed-metal sulfide (MMS) catalysts. The MMS catalyst can be any mixed metal sulfide catalyst that is self-supported or unsupported. These catalysts have a high level of activity. In one embodiment, the MMS catalyst is a self-supported multi-metallic catalyst prepared from a precursor in the oxide or hydroxide form. In a preferred embodiment, the precursor is in the hydroxide form.

The third and the fifth zones, below the second and fourth zones, respectively, are hydrocracking zones. Each hydrocracking zone involves hydrocracking the feed to reduce the boiling point of the feed.

The fourth and sixth zones, below the third and fifth zones, respectively, are hydrotreating zones, wherein the hydrotreatment is carried out by one or more self-supported hydrotreating catalysts.

In certain embodiments, the layered catalyst reactor system comprises an additional hydrocracking zone, followed by an additional self-supported catalyst hydrotreatment zone (sixth and seventh zones).

The final zone (either seventh or ninth) is a post-treatment zone or an additional hydrotreatment zone, wherein the hydrotreatment occurs in the layers comprising one or more self-supported hydrotreating catalysts.

Generally, the hydrocarbon feedstock is introduced into the first zone (i.e. top layer) of the layered catalyst reactor system to produce treated effluent. Hydrogen is also introduced into the layered catalyst reactor system to facilitate the hydrogenation reactions. The treated effluent from each layer moves to the next layer of the layered catalyst reactor system in a downward path. In this manner, the initial hydrocarbon feedstock and resulting treated effluent from each layer is passed through the layered catalyst reactor system.

In certain embodiments, the operating temperature of the layered catalyst reactor system is in the range of about 715 to about 760° F., or about 700 to about 775° F.

The weight hourly space velocity (WHSV) is defined as the weight of feed flowing per unit weight of the catalyst per hour operating conditions of the reactor. In certain embodiments, the WHSV is in the range of about 0.41 to about 1.1, or about 0.4 to about 1.1 h$^{-1}$.

The liquid hourly space velocity (LHSV) is the ratio of liquid volume flow per hour to catalyst volume. In certain embodiments, the LHSV is in the range of about 0.39 to about 0.81, or about 0.3 to about 0.9 h$^{-1}$.

In certain embodiments, the total pressure in the layered catalyst reactor system during operation is about 2318 to about 2350 psig, or about 2310 to about 2360 psig.

In certain embodiments, the inlet hydrogen pressure in the layered catalyst reactor system during operation is about 2244 to about 2310 psia, or about 2240 to about 2320 psia.

In certain embodiments, the gas rate in the layered catalyst reactor system during operation is about 7512 to about 8040 scfb, or about 7500 to about 8100 scfb.

In certain embodiments, the normalized temperature of the layered catalyst reactor system remains less than about 770° F. or less than about 765° F. during the hydrotreatment reaction.

Demetallization Catalysts

Metal contaminants, such as vanadium and nickel contaminants, are removed from hydrocarbon feedstocks through contact with one or more demetallization catalysts. Generally, the demetallization catalyst according to the embodiments can be a conventional demetallization catalyst known in the art. Examples of demetallization catalysts (i.e., hydrodemetallization catalysts) include but are not limited to: those prepared from synthetic aluminum oxide or natural aluminum silicate enriched with the oxides of molybdenum, cobalt and nickel, for example nickel oxide-molybdenum oxide, cobalt oxide, molybdenum oxide, nickel oxide-tungsten oxide, all on alumina; and bauxite promoted with iron, cobalt, molybdenum, nickel, zinc, and manganese.

In certain embodiments, the demetallization catalyst is a catalyst comprising, for example ICR 132 (available from Advanced Refining Technologies LLC).

In certain embodiments, the supported hydrotreatment catalyst layer comprises or consists of one type of supported hydrotreatment catalyst. In certain embodiments, the supported hydrotreatment catalyst layer comprises or consists of two type of supported hydrotreatment catalyst.

Supported Hydrotreating Catalysts

Generally, the supported hydrotreating catalyst according to the embodiments can be a conventional hydrotreating (e.g., hydrodesulfurization) catalyst known in the art. Examples of supported hydrotreating catalysts include but are not limited to: catalysts comprised of at least one Group VIII metal, such as iron, cobalt or nickel; and at least one Group VIB metal, such as molybdenum or tungsten; on a relatively high surface area support material, for example alumina. Other suitable catalyst supports include zeolites, amorphous silica-alumina, and titania-alumina. In certain embodiment, the supported hydrotreatment catalysts comprise noble metals, such as Pd and Pt. More than one type of hydrotreatment catalyst can be used in the same or different beds of the layered catalyst reactor systems. In certain embodiments, the Group VIII metal is typically present in an amount ranging from about 2 to about 20 wt. %, or from about 4 to about 12 wt. %. The Group VIB metal will typically be present in an amount ranging from about 5 to about 50 wt. %, from about 10 to about 40 wt. %, or from about 20 to about 30 wt. %. All metal weight percentages are on support (percentages based on the weight of the support).

In certain embodiments, the supported hydrotreating catalyst comprises one or more Group VIII metals selected from iron, cobalt or nickel. In certain embodiments, the supported hydrotreating catalyst comprises one or more Group VIII metals selected from cobalt and nickel. In certain embodiments, the supported hydrotreating catalyst comprises cobalt.

In certain embodiments, the supported hydrotreating catalyst comprises support material selected from alumina, zeolites, amorphous silica-alumina, and titania-alumina.

In certain embodiments, the supported hydrotreating catalyst is a catalyst comprising nickel and molybdenum. In certain embodiments, the supported hydrotreating catalyst is a catalyst comprising nickel oxide and molybdenum trioxide, for example ICR 513 (available from Advanced Refining Technologies LLC).

In certain embodiments, the supported hydrotreatment catalyst layer comprises or consists of one type of supported hydrotreatment catalyst. In certain embodiments, the supported hydrotreatment catalyst layer comprises or consists of two types of supported hydrotreatment catalyst.

Hydrocracking Catalysts

Hydrocracking catalysts suitable for use in the systems and processes described herein include but are not limited to catalysts that include cracking activity, for example catalysts containing crystalline aluminosilicates. Generally, the hydrocracking catalyst according to the embodiments can be a conventional hydrocracking catalyst known in the art. Examples of hydrocracking catalysts include, but are not limited to: catalysts comprising nickel, nickel-cobalt-molybdenum, cobalt-molybdenum and nickel-tungsten and/or nickel-molybdenum, the latter two of which are preferred. Non-limiting examples of noble metal catalysts include those based on platinum and/or palladium. Porous support materials which may be used for both the noble and non-noble metal catalysts comprise a refractory oxide material such as alumina, silica, alumina-silica, kieselguhr, diatomaceous earth, magnesia, or zirconia, with alumina, silica, alumina-silica being preferred and the most common. Zeolitic supports, especially the large pore faujasites such as ultrastable Y (USY) can also be used.

A large number of hydrocracking catalysts are available from different commercial suppliers and may be used according to feedstock and product requirements; their functionalities may be determined empirically. Any catalyst with the desired hydroconversion functionality at the selected operating conditions can be used, including conventional hydrocracking catalysts.

In certain embodiments, the hydrocracking catalysts are not the same catalysts used for the demetallization, supported hydrotreating or unsupported hydrotreating catalyst layers.

In certain embodiments, the hydrocracking catalyst comprises nickel, cobalt, molybdenum and/or tungsten. In certain embodiments, the hydrocracking catalyst comprises nickel. In certain embodiments, the hydrocracking catalyst comprises nickel-cobalt-molybdenum. In certain embodiments, the hydrocracking catalyst comprises cobalt-molybdenum. In certain embodiments, the hydrocracking catalyst comprises nickel-tungsten. In certain embodiments, the hydrocracking catalyst comprises nickel-molybdenum.

In certain embodiments, the hydrocracking catalyst comprises support material selected from a refractory oxide material such as alumina, silica, alumina-silica, kieselguhr, diatomaceous earth, magnesia, or zirconia, with alumina, silica, or alumina-silica; and zeolitic supports, for example the large pore faujasites such as USY.

In certain embodiments, the hydrocracking catalyst is a catalyst comprising nickel and molybdenum or nickel and tungsten, for example ICR 250 (available from Advanced Refining Technologies LLC).

In certain embodiments, the hydrocracking catalyst is a supported hydrocracking catalyst. In certain embodiments, the hydrocracking catalyst layer comprises or consists of one type of hydrocracking catalyst. In certain embodiments, the hydrocracking catalyst layer comprises or consists of two types of hydrocracking catalyst.

Self-Supported Hydrotreating Catalyst

In certain embodiments, the self-supported hydrotreating catalysts are unsupported hydrotreating catalysts, i.e. are not supported on, or affixed to, other materials. Generally, the self-supported hydrotreating catalysts have higher levels of activity by volume than supported hydrotreating catalyst.

Examples of self-supported (or unsupported) hydrotreating catalysts include but are not limited to: unsupported multi-metallic catalysts prepared by sulfiding a catalyst of a precursor of the formula.

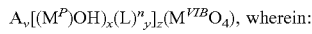

$A_v[(M^P)OH)_x(L)"_y]_z(M^{VIB}O_4)$, wherein:

A is one monovalent cationic species $M^P$ is a promoter metal with an oxidation state of +2 or +4 selected from one or more of Group IIA, Group IIB, Group IVA, and Group VIII metals (especially a Group VIII, such as Ni)

L is an organic oxygen-containing ligand (e.g., maleate) and $M^{VIB}$ is a Group VIB metal (e.g., one or more of Mo, W).

An important aspect of the catalyst precursor (prior to sulfidation) is that it is in the hydroxide form.

In one embodiment, L is selected from carboxylates, carboxylic acids, aldehydes, ketones, the enolate forms of aldehydes, the enolate forms of ketones, and hemiacetals, and combinations thereof.

In one embodiment, A is selected from monovalent cations such as $NH_M^+$, other quaternary ammonium ions, organic phosphonium cations, alkali metal cations, and combinations thereof.

In one embodiment where both molybdenum and tungsten are used as the Group VIB metals, the molybdenum to tungsten atomic ratio (Mo:W) is in the range of about 10:1 to 1:10. In another embodiment, the ratio of Mo:W is between about 1:1 and 1:5. In an embodiment where molybdenum and tungsten are used as the Group VIB metals, the charge-neutral catalyst precursor is of the formula $A_v[(M^P)(OH)_x(L)"_y]_z(Mo_tW_rO_4)$. In yet another embodiment, where molybdenum and tungsten are used as the Group VIB metals, chromium can be substituted for some or all of the tungsten with the ratio of (Cr+W):Mo is in the range of about 10:1 to 1:10. In another embodiment, the ratio of (Cr+W):Mo is between 1:1 and 1:5. In an embodiment where molybdenum, tungsten, and chromium are the Group VIB metals, the charge-neutral catalyst precursor is of the formula $A_v[(M^P)(OH)_x(L)"_y]_z(Mo_tW_rCr_rO_4)$.

In one embodiment, the Promoter metal $M^P$ is at least a Group VIII metal with $M^P$ having an oxidation state of +2 and the catalyst precursor of the formula $A_v[(M^P)(OH)_x(L)"_y]_z(M^{VIB}O_4)$ wherein (v−2+2z−x*z+n*y*z)=0.

In one embodiment, the Promoter metal $M^P$ is a mixture of two Group VIII metals such as Ni and Co. In yet another embodiment, $M^P$ is a combination of three metals such as Ni, Co and Fe.

In one embodiment where $M^P$ is a mixture of two group IIB metals such as Zn and Cd, the charge-neutral catalyst precursor is of the formula $A_v[(Zn_aCd_{a'})(OH)_x(L)_y]_z(M^{VIB}O_4)$. In yet another embodiment, where $M^P$ is a combination of three metals such as Zn, Cd and Hg, the charge-neutral catalyst precursor is of the formula $A_v[(Zn_aCd_{a'}Hg_{a''})(OH)_x(L)"_y]_z(M^{VIB}O_4)$.

In one embodiment wherein $M^P$ is a mixture of two Group IVA metals such as Ge and Sn, the charge-neutral catalyst precursor is of the formula $A_v[(Ge_bSn_{b'})(OH)_x(L)"_y]_z(M^{VIB}O_4)$. In another embodiment wherein $M^P$ is a combination of three Group IVA metals such as Ge, Sn, and Pb, the charge-neutral catalyst precursor is of the formula $A_v[(Ge_bSn_{b'}Pb_{a''})(OH)_x(L)"_y]_z(M^{VIB}O_4)$.

Promoter Metal Component $M^P$: In one embodiment, the source for the Promoter metal ($M^P$) compound is in a solution state, with the whole amount of the Promoter metal compound dissolved in a liquid to form a homogeneous solution. In another embodiment, the source for the Promoter metal is partly present as a solid and partly dissolved in the liquid. In a third embodiment, it is completely in the solid state.

The Promoter metal compound $M^P$ can be a metal salt or mixtures of metal salts selected from nitrates, hydrated nitrates, chlorides, hydrated chlorides, sulfates, hydrated sulfates, carbonates, formates, acetates, oxalates, citrates, maleates, fumarate, phosphates, hypophosphites, and mixtures thereof.

In one embodiment, the Promoter metal $M^P$ is a nickel compound which is at least partly in the solid state, e.g., a water-insoluble nickel compound such as nickel carbonate, nickel hydroxide, nickel phosphate, nickel phosphite, nickel formate, nickel fumarate, nickel sulfide, nickel molybdate, nickel tungstate, nickel oxide, nickel alloys such as nickel-molybdenum alloys, Raney nickel, or mixtures thereof.

In one embodiment, the Promoter metal $M^P$ is selected from the group of IIB and VIA metals such as zinc, cadmium, mercury, germanium, tin or lead, and combinations thereof, in their elemental, compound, or ionic form. In yet another embodiment, the Promoter metal $M^P$ further comprises at least one of Ni, Co, Fe and combinations thereof, in their elemental, compound, or ionic form.

In one embodiment, the Promoter metal compound is a zinc compound which is at least partly in the solid state, e.g., a zinc compound poorly soluble in water such as zinc carbonate, zinc hydroxide, zinc phosphate, zinc phosphite, zinc formate, zinc fumarate, zinc sulfide, zinc molybdate, zinc tungstate, zinc oxide, zinc alloys such as zinc-molybdenum alloys.

In an embodiment, the Promoter metal is a Group IIA metal compound, selected from the group of magnesium, calcium, strontium and barium compounds which are at least partly in the solid state, e.g., a water-insoluble compound such as a carbonate, hydroxide, fumarate, phosphate, phosphite, sulfide, molybdate, tungstate, oxide, or mixtures thereof.

In one embodiment, the Promoter metal compound is a tin compound which is at least partly in the solid state, e.g., a tin compound poorly soluble in water such as stannic acid, tin phosphate, tin formate, tin acetate, tin molybdate, tin tungstate, tin oxide, tin alloys such as tin-molybdenum alloys.

Group VIB Metal Component: The Group VIB metal ($M^{VIB}$) compound can be added in the solid, partially dissolved, or solution state. In one embodiment, the Group VIB metal compound is selected from molybdenum, chromium, tungsten compounds, and combinations thereof. Examples of such compounds include, but are not limited to, alkali metal, alkaline earth, or ammonium metallates of molybdenum, tungsten, or chromium, (e.g., ammonium tungstate, meta-, para-, hexa-, or polytungstate, ammonium chromate, ammonium molybdate, iso-, peroxo-, di-, tri-, tetra-, hepta-, octa-, or tetradecamolybdate, alkali metal heptamolybdates, alkali metal orthomolybdates, or alkali metal isomolybdates), ammonium salts of phosphomolybdic acids, ammonium salts of phosphotungstic acids, ammonium salts of phosphochromic acids, molybdenum (di- and tri) oxide, tungsten (di- and tri) oxide, chromium or chromic oxide, molybdenum carbide, molybdenum nitride, aluminum molybdate, molybdic acid, chromic acid, tungstic acid, Mo—P heteropolyanion compounds, Wo-Si heteropolyanion compounds, W—P heteropolyanion compounds. W—Si heteropolyanion compounds, Ni—Mo—W heteropolyanion compounds, Co—Mo—W heteropolyanion compounds, or mixtures thereof, added in the solid, partially dissolved, or solute state.

Chelating Agent (Ligand) L: In one embodiment, the catalyst precursor composition comprises at least a non-toxic organic oxygen-containing ligand with an LD50 (as single oral dose to rats) of greater than 500 mg/kg. In a second embodiment, the organic oxygen-containing ligand L has an LD50 of >700 mg/kg. In a third embodiment, organic oxygen-containing chelating agent has an LD50 of >1000 mg/kg. As used herein, the term "non-toxic" means the ligand has an LD50 (as single oral dose to rats) of greater than 500 mg/kg. As used herein the term "at least an organic oxygen containing ligand" means the composition may have more than one organic oxygen-containing ligand in some embodiments, and some of the organic oxygen-containing ligand may have an LD50 of <500 mg/kg, but at least one of the organic-oxygen containing ligands has an LD50 of >500 mg/kg.

In one embodiment, the oxygen-containing chelating agent L is selected from the group of non-toxic organic acid addition salts such as formic acid, acetic acid, propionic acid, maleic acid, fumaric acid, succinic acid, tartaric acid, citric acid, oxalic acid, glyoxylic acid, aspartic acid, alkane sulfonic acids such as methanesulfonic acid and ethanesulfonic acid, arylsulfonic acids such as benzenesulfonic acid and p-toluenesulfonic acid and arylcarboxylic acids such as benzoic acid. In one embodiment, the oxygen-containing chelating agent L is maleic acid (LD50 of 708 mg/kg).

In another embodiment, the non-toxic chelating agent L is selected from the group of glycolic acid (having an LD50 of 1950 mg/kg), lactic acid (LD50 of 3543 mg/kg), tartaric acid (LD50 of 7500 mg/kg), malic acid (LD50 of 1600 mg/kg), citric acid (LD50 of 5040 mg/kg), gluconic acid (LD50 of 10380 mg/kg), methoxy-acetic acid (LD50 of 3200 mg/kg), ethoxy-acetic acid (LD50 of 1292 mg/kg), malonic acid (LD50 of 1310 mg/kg), succinic acid (LD50 of 500 mg/kg), fumaric acid (LD50 of 10700 mg/kg), and glyoxylic (LD50 of 3000 mg/kg). In yet another embodiment, the non-toxic chelating agent is selected from the group of organic sulfur compounds including but not limited to mercapto-succinic acid (LD50 of 800 mg/kg) and thio-diglycolic acid (LD50 of 500 mg/kg).

In yet another embodiment, the oxygen containing ligand L is a carboxylate containing compound. In one embodiment, the carboxylate compound contains one or more carboxylate functional groups. In yet another embodiment, the carboxylate compound comprises monocarboxylates including, but not limited to, formate, acetate, propionate, butyrate, pentanoate, and hexanoate and dicarboxylates including, but not limited to, oxalate, malonate, succinate, glutarate, adipate, malate, maleate, fumarate, and combinations thereof. In a fourth embodiment, the carboxylate compound comprises maleate.

The organic oxygen containing ligands can be mixed with the Promoter metal containing solution or mixture, the Group VIB metal containing solution or mixture, or a combination of the Promoter metal and Group VIB metal containing precipitates, solutions, or mixtures. The organic oxygen containing ligands can be in a solution state, with the whole amount of the organic oxygen containing ligands dissolved in a liquid such as water. The organic oxygen containing ligands can be partially dissolved and partially in the solid state during mixing with the Promoter metal(s), Group VIB metal(s), and combinations thereof.

Diluent Component: The term diluent may be used interchangeably with binder. The use of diluent is optional in the making of the catalyst precursor.

In one embodiment, a diluent is included in the process for making the catalyst precursor composition. Generally, the diluent material to be added has less catalytic activity than the catalyst prepared from the catalyst precursor composition (without the diluent) or no catalytic activity at all. In one embodiment, by adding a diluent, the activity of the catalyst can be reduced. Therefore, the amount of diluent to be added in the process generally depends on the desired activity of the final catalyst composition. Diluent amounts from 0-95 wt. % of the total composition can be suitable, depending on the envisaged catalytic application.

The diluent can be added to the Promoter metal component(s), Promoter metal containing mixtures, Group VIB metal(s) or metal containing mixtures either simultaneously or one after the other. Alternatively, the Promoter metal and Group VIB metal mixtures can be combined together, and subsequently a diluent can be added to the combined metal mixtures. It is also possible to combine part of the metal mixtures either simultaneously or one after the other, to subsequently add the diluent and to finally add the rest of the metal mixtures either simultaneously or one after the other. Furthermore, it is also possible to combine the diluent with metal mixtures in the solute state and to subsequently add a metal compound at least partly in the solid state. The organic oxygen containing ligand is present in at least one of the metal-containing mixtures.

In one embodiment, the diluent is composited with a Group VIB metal and/or a Promoter metal, prior to being composited with the bulk catalyst precursor composition and/or prior to being added during the preparation thereof. Compositing the diluent with any of these metals in one embodiment is carried out by impregnation of the solid diluent with these materials.

Diluent materials include any materials that are conventionally applied as a diluent or binder in hydroprocessing catalyst precursors. Examples include silica, silica-alumina, such as conventional silica-alumina, silica-coated alumina and alumina-coated silica, alumina such as (pseudo)boehmite, or gibbsite, titania, zirconia, cationic clays or anionic clays such as saponite, bentonite, kaolin, sepiolite or hydrotalcite, or mixtures thereof. In one embodiment, binder materials are selected from silica, colloidal silica doped with aluminum, silica-alumina, alumina, titania, zirconia, or mixtures thereof.

These diluents can be applied as such or after peptization. It is also possible to apply precursors of these diluents that, during the process, are converted into any of the above-described diluents. Suitable precursors are, e.g., alkali metal or ammonium aluminates (to obtain an alumina diluent), water glass or ammonium- or acid-stabilized silica sols (to obtain a silica diluent), a mixture of aluminates and silicates (to obtain a silica alumina diluent), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

Other Optional Components: If desired, other materials, including other metals can be added in addition to the components described above. These materials include any material that is added during conventional hydroprocessing catalyst precursor preparation. Suitable examples are phosphorus compounds, boron compounds, additional transition metals, rare earth metals, fillers, or mixtures thereof. Suitable phosphorus compounds include ammonium phosphate, phosphoric acid, or organic phosphorus compounds. Phosphorus compounds can be added at any stage of the process steps. Suitable additional transition metals that can be added to the process steps include are, e.g., rhenium, ruthenium, rhodium, iridium, chromium, vanadium, iron, cobalt, nickel, zinc, platinum, palladium, cobalt, etc. In one embodiment, the additional metals are applied in the form of water-insoluble compounds. In another embodiment, the additional metals are added in the form of water-soluble compounds. Apart from adding these metals during the process, it is also possible to composite the final catalyst precursor composition with the optional materials. It is, e.g., possible to impregnate the final catalyst precursor composition with an impregnation solution comprising any of these additional materials.

Methods for Making Hydroprocessing Catalyst Precursor: The preparation method allows systematic varying of the composition and structure of the catalyst precursor by controlling the relative amounts of the elements, the types of the reagents, and the length and severity of the various reactions and reaction steps.

The order of addition of the reagents used in forming the catalyst precursor is not important. For example, organic oxygen containing ligand can be combined with a mixture of Promoter metal(s) and Group VIB metal(s) prior to precipitation or cogelation. The organic oxygen containing ligand can be mixed with a solution of a Promoter metal, and then added to a solution of one or more Group VIB metals. The organic oxygen containing ligand can be mixed with a solution of one or more Group VIB metals and added to a solution of one or more Promoter metals.

Forming a Precipitate or Cogel with Group VIB/Promoter Metals: In one embodiment of the process, the first step is a precipitation or cogelation step, which involves reacting in a mixture the Promoter metal component(s) in solution and the Group VIB metal component in solution to obtain a precipitate or cogel. The precipitation or cogelation is carried out at a temperature and pH which the Promoter metal compound and the Group VIB metal compound precipitate or form a cogel. An organic oxygen containing ligand in solution or at least partially in solution is then combined with the precipitate or cogel to form an embodiment of the catalyst precursor.

In an embodiment, the temperature at which the catalyst precursor is formed is between 50-150° C. If the temperature is below the boiling point of the protic liquid, such as 100° C. in the case of water, the process is generally carried out at atmospheric pressure. Above this temperature, the reaction is generally carried out at increased pressure, such as in an autoclave. In one embodiment, the catalyst precursor is formed at a pressure between 0 to 3000 psig. In a second embodiment, between 100 to 1000 psig.

The pH of the mixture can be changed to increase or decrease the rate of precipitation or cogelation, depending on the desired characteristics of the product. In one embodiment, the mixture is kept at its natural pH during the reaction step(s). In another embodiment, the pH is maintained in the range of 0-12. In another embodiment, between 4-10. In a further embodiment, the pH ranges between 7-10. Changing the pH can be done by adding base or acid to the reaction mixture, or adding compounds, which decompose upon temperature increase into hydroxide ions or $H^+$ ions that respectively increase or decrease the pH. Examples include urea, nitrites, ammonium hydroxide, mineral acids, organic acids, mineral bases, and organic bases.

In one embodiment, the reaction of Promoter metal component(s) is carried out with water-soluble metal salts, e.g., zinc, molybdenum and tungsten metal salts. The solution can further comprise other Promoter metal component(s), e.g., cadmium or mercury compounds such as $Cd(NO_3)_2$ or $(CH_3CO_2)_2Cd$, Group VIII metal components including cobalt or iron compounds such as $Co(NO_3)_2$ or $(CH_3CO_2)_2Co$, as well as other Group VIB metal component(s) such as chromium.

In one embodiment, the reaction of Promoter metal component(s) is carried out with water-soluble tin, molybdenum and tungsten metal salts. The solution can further comprise other Group IVA metal component(s), e.g. lead compounds such as $Pb(NO_3)_4$ or $(CH_3CO_2)_2Pb$, as well as other Group VIB metal compounds such as chromium compounds.

The reaction is carried with the appropriate metal salts resulting in precipitate or cogel combinations of zinc/molybdenum/tungsten, tin/molybdenum/tungsten, zinc/molybdenum, zinc/tungsten, tin/molybdenum, tin/tungsten, or zinc/tin/molybdenum/tungsten, or nickel/molybdenum/tungsten, cobalt/molybdenum/tungsten, nickel/molybdenum, nickel/tungsten, cobalt/molybdenum, cobalt/tungsten, or nickel/cobalt/molybdenum/tungsten. An organic oxygen containing ligand can be added prior to or after precipitation or cogelation of the Promoter metal compounds and/or Group VIB metal compounds.

The metal precursors can be added to the reaction mixture in solution, suspension or a combination thereof. If soluble salts are added as such, they will dissolve in the reaction mixture and subsequently be precipitated or cogeled. The solution can be heated optionally under vacuum to effect precipitation and evaporation of the water.

After precipitation or cogelation, the catalyst precursor can be dried to remove water. Drying can be performed under atmospheric conditions or under an inert atmosphere such as nitrogen, argon, or vacuum. Drying can be effected at a temperature sufficient to remove water but not to remove organic compounds. Preferably drying is performed at about 120° C. until a constant weight of the catalyst precursor is reached.

Forming a Precipitate with Optional Binder Component(s): In one embodiment with the use of a binder, the binder components can be added to the reaction mixture containing the metal precursors in solution, suspension or a combination thereof, forming precipitation or cogelation. The precipitate is subsequently dried to remove water.

In one embodiment with the use of magnesium aluminosilicate clay as a binder, a first reaction mixture is formed comprising a silicon component, an aluminum component, a magnesium component, the Promoter metal compounds and/or Group VIB metal compounds. In one embodiment, the first reaction mixture is formed under ambient pressure and temperature conditions. In one embodiment, the reaction is under a pressure ranging from 0.9 bar and 1.2 bar, and a temperature between about 0° C. and 100° C.

Examples of silicon components include, but are not limited to sodium silicate, potassium silicate, silica gels, silica sols, hydronium- or ammonium-stabilized silica sols, and combinations thereof. Examples of aluminum components aluminum useful in the process of the present invention include, but are not limited to, sodium aluminate, potassium aluminate, aluminum sulfate, aluminum nitrate, and combinations thereof. Examples of magnesium components useful in the process of the present invention include, but are not limited to, magnesium metal, magnesium hydroxide, magnesium halides, magnesium sulfate, and magnesium nitrate. In one embodiment, a sufficient amount of an acid is added to the mixture containing the metal precursors and the binder components to adjust the pH of the mixture to about 1 to about 6, forming a first reaction mixture.

After the formation of the first reaction mixture, an alkali base is added to form a second reaction mixture. Examples of alkali base include, but are not limited to, ammonium hydroxide, sodium hydroxide and potassium hydroxide. Sufficient alkali base is added to the first reaction mixture for the pH of the resulting second reaction mixture between about 7 to about 12. The second reaction mixture is then reacted for sufficient time and at sufficient temperature to form a catalyst precursor incorporating at least a clay as a binder. In embodiments, the time is at least one second. In a second embodiment, 15 minutes. A third embodiment, at least 30 minutes. The temperature of the second reaction mixture can range from about 0° C. to about 100° C. The reaction can be done at ambient pressure, although higher or lower pressures are not excluded.

In one embodiment with magnesium aluminosilicate clay as a binder, the ratio of silicon to aluminum to magnesium can be expressed in terms of elemental mole ratios: aSi:bAl:cMg. wherein "a" has a value from 3 to 8, "b" has a value from 0.6 to 1.6, and "c" has a value of from 3 to 6.

Characterization of the Catalyst precursor: Characterization of the charge-neutral catalyst precursor can be performed using techniques known in the art, including, but not limited to, powder x-ray diffraction (PXRD), elemental analysis, surface area measurements, average pore size distribution, average pore volume. Porosity and surface area measurements can be performed using BJH analysis under B.E.T. nitrogen adsorption conditions.

Characteristics of the Catalyst precursor: In one embodiment, the catalyst precursor has an average pore volume of 0.05-5 mL/g as determined by nitrogen adsorption. In another embodiment, the average pore volume is 0.1-4 mL/g. In a third embodiment, 0.1-3 mL/g.

In one embodiment, the catalyst precursor has a surface area of at least 10 $m^2/g$. In a second embodiment, a surface area of at least 50 $m^2/g$. In a third embodiment, a surface area of at least 150 $m^2/g$.

In one embodiment, the catalyst precursor has an average pore size, as defined by nitrogen adsorption, of 2-50 nanometers. In a second embodiment, an average pore size of 3-30 nanometers. In a third embodiment, an average pore size of 4-15 nanometers.

In one embodiment with the inclusion of magnesium aluminosilicate clay as a binder, the catalyst precursor is a layered material composed of a stack of elemental clay platelets.

Shaping Process: In one embodiment, the catalyst precursor composition can generally be directly formed into various shapes depending on the intended commercial use. These shapes can be made by any suitable technique, such as by extrusion, pelletizing, beading, or spray drying. If the amount of liquid of the bulk catalyst precursor composition is so high that it cannot be directly subjected to a shaping step, a solid-liquid separation can be performed before shaping.

Addition of Pore-forming Agents: The catalyst precursor can be mixed with a pore forming agent including, but not limited to steric acid, polyethylene glycol polymers, carbohydrate polymers, methacrylates, and cellulose polymers. For example, the dried catalyst precursor can be mixed with cellulose containing materials such as methylcellulose, hydroxypropyl cellulose, or other cellulose ethers in a ratio of between 100:1 and 10:1 (wt. % catalyst precursor to wt. % cellulose) and water added until a mixture of extrudable consistency is obtained. Examples of commercially available cellulose based pore forming agents include but are not limited to: METHOCEL™ (available from DuPont), Avicel© (available from DuPont), and Porocel (available from Evonik). The extrudable mixture can be extruded and then optionally dried. In one embodiment, the drying can be performed under an inert atmosphere such as nitrogen, argon, or vacuum. In another embodiment, the drying can be performed at elevated temperatures between 70 and 200° C. In yet another embodiment, the drying is performed at 120° C.

Sulfiding Agent Component: The charge-neutral catalyst precursor can be sulfided to form an active catalyst. In one embodiment, the sulfiding agent is elemental sulfur by itself. In another embodiment, the sulfiding agent is a sulfur-containing compound which under prevailing conditions, is decomposable into hydrogen sulfide. In yet a third embodiment, the sulfiding agent is $H_2S$ by itself or $H_2S$ in $H_2$.

In one embodiment, the sulfiding agent is selected from the group of ammonium sulfide, ammonium polysulfide $((NH_4)_2S_x)$, ammonium thiosulfate $((NH_4)_2S_2O_3)$, sodium thiosulfate $(Na_2S_2O_3)$, thiourea $(NH_2CSNH_2)$, carbon disulfide, dimethyl disulfide (DMDS), dimethyl sulfide (DMS), mercaptans, di-tert-butyl polysulfide (TBPS), tert-nonyl polysulfide (TNPS), and the like. In another embodiment, the sulfiding agent is selected from alkali- and/or alkaline earth metal sulfides, alkali- and/or alkaline earth metal hydrogen sulfides, and mixtures thereof. The use of sulfiding agents containing alkali- and/or alkaline earth metals can require an additional separation process step to remove the alkali- and/or alkaline earth metals from the spent catalyst.

In one embodiment, the sulfiding agent is ammonium sulfide in aqueous solution, which aqueous ammonium sulfide solution can be synthesized from hydrogen sulfide and ammonia refinery off-gases. This synthesized ammonium sulfide is readily soluble in water and can easily be stored in aqueous solution in tanks prior to use. In one embodiment wherein the sulfidation is with an aqueous ammonium sulfide solution, and also in the presence of at least a sulfur additive selected from the group of thiadiazoles, thioacids, thioamides, thiocyanates, thioesters, thiophenols, thiosemicarbazides, thioureas, mercapto alcohols, and mixtures thereof.

In one embodiment, hydrocarbon feedstock is used as a sulfur source for performing the sulfidation of the catalyst precursor. Sulfidation of the catalyst precursor by a hydrocarbon feedstock can be performed in one or more hydrotreating reactors during hydrotreatment.

In one embodiment, the sulfiding agent is present in an amount in excess of the stoichiometric amount required to form the sulfided catalyst from the catalyst precursor. In another embodiment, the amount of sulfiding agent represents a sulfur to Group VIB metal mole ratio of at least 3 to 1 to produce a sulfided catalyst from the catalyst precursor. In a third embodiment, the total amount of sulfur-containing compound is generally selected to correspond to any of about 50-300%, 70-200%, and 80-150%, of the stoichiometric sulfur quantity necessary to convert the metals into for example, $Co_9S_8$, $MoS_2$, $WS_2$, $Ni_3S_2$, etc.

Sulfiding Step: Sulfiding (sometimes referred to as "pre-sulfiding") of the catalyst precursor to form the catalyst can be performed prior to introduction of the catalyst into a hydrotreating reactor (thus ex-situ sulfiding). In another embodiment, the sulfiding is in-situ. In one embodiment with the sulfiding process being done ex-situ, the formation of undesirable compounds in the hydrotreating unit is prevented. In one embodiment, the catalyst precursor is converted into an active catalyst upon contact with the sulfiding agent at a temperature ranging from 70° C. to 500° C., from 10 minutes to 15 days, and under a $H_2$-containing gas pressure. If the sulfidation temperature is below the boiling point of the sulfiding agent, such as 60-70° C. in the case of ammonium sulfide solution, the process is generally carried out at atmospheric pressure. Above the boiling temperature of the sulfiding agent/optional components, the reaction is generally carried out at an increased pressure.

In one embodiment, the sulfiding can be carried out in the gaseous phase with hydrogen and a sulfur-containing compound which is decomposable into $H_2S$. Examples include mercaptans, $CS_2$, thiophenes, DMS, DMDS and suitable S-containing refinery outlet gasses. The use of $H_2S$ alone is sufficient. The contacting between the catalyst precursor in gaseous phase with hydrogen and a sulfur-containing compound can be done in one step at a temperature between 125° C. to 450° C. (257° F. to 842° F.) in one embodiment, and between 225° C. to 400° C. (437° F. to 752° F.) in another embodiment. In one embodiment, the sulfidation is carried out over a period of time with the temperature being increased in increments, e.g., from 0.5 to 4° C. (0.9 to 7.2° F.) per min. and held over a period of time, e.g., from 1 to 12 hours, until completion.

As used herein, completion of the sulfidation process means that at least 95% of stoichiometric sulfur quantity necessary to convert the metals into for example, $Co_9S_8$, $MoS_2$, $WS_2$, $Ni_3S_2$, etc., has been used up.

In another embodiment of sulfidation in the gaseous phase, the sulfidation is done in two or more steps, with the first step being at a lower temperature than the subsequent step(s). For example, the first step is at about 100 to 250° C. (212° F. to 482° F.), preferably about 125 to 225° C. (257° F. to 437° F.). After a short period of time, e.g., from ½ to 2 hours (temperature kept at a plateau). The second step can be carried out at about 225 to 450° C. (437° F. to 842° F.), and preferably about 250 to 400° C. (482° F. to 752° F.). The total pressure during the sulfidation step can be between atmospheric and about 10 bar (1 MPa). The gaseous mixture of $H_2$ and sulfur containing compound can be the same or different in the steps. The sulfidation in the gaseous phase can be done in any suitable manner, including a fixed bed process and a moving bed process (in which the catalyst moves relative to the reactor, e.g., ebulliated process and rotary furnace).

In one embodiment, the sulfidation is carried out in the liquid phase. At first, the catalyst precursor is brought in contact with an organic liquid in an amount in the range of 20-500% of the catalyst precursor pore volume. The contacting with the organic liquid can be at a temperature ranging from ambient to 250° C. (482° F.). After the incorporation of an organic liquid, the catalyst precursor is brought into contact with hydrogen and a sulfur-containing compound.

In one embodiment, the organic liquid has a boiling range of about 100-550° C. (212-1022° F.). In another embodiment, the organic liquid is a petroleum fraction such as heavy oils, lubricating oil fractions like mineral lube oil, atmospheric gas oils, vacuum gas oils, straight run gas oils, white spirit, middle distillates like diesel, jet fuel and heating oil, naphthas, and gasoline. In one embodiment, the organic liquid contains less than 10 wt. % sulfur, and preferably less than 5 wt. %.

In one embodiment, the sulfidation (or "start-up") in the liquid phase is done as a "quick" process, with the sulfidation taking place over a period of less than 72 hours and with the ramp-up in temperature ranges from 0.5 to 4° C. (0.9 to 7.2° F.) per min. In a second embodiment, the quick start-up takes less than 48 hours. In a third embodiment, less than 24 hours.

In the quick sulfidation, the contacting between the catalyst precursor in organic liquid with hydrogen and a sulfur-containing compound can be done in one step at a temperature between 150 to 450° C. in one embodiment, and between 225° C. to 400° C. in another embodiment. In yet another embodiment of the quick sulfidation, the sulfidation is done in two or more steps, with the first step being at a lower temperature than the subsequent step(s). For example, the first step is at about 100 to 250° C. (212° F. to 482° F.), or from 125 to 225° C. (257° F. to 437° F.). After a short period of time, e.g., from 0.5 to 2 hours (temperature kept at a plateau), then the temperature is ramped up for the second step, e.g., from 250 to 450° C. (482° F. to 842° F.), and preferably from 225 to 400° C. (437° F. to 7520° F.). The temperature is maintained from 1 to 36 hours, after which time sulfidation is complete.

In yet another embodiment, the sulfidation in the liquid phase is done as a "slow" process, with the sulfidation taking place over a period of time from four (4) days up to three weeks, i.e., at least 96 hours. In this slow process, the contacting between the catalyst precursor in organic liquid with hydrogen and a sulfur-containing compound is done in two or more steps, with the first step being at a lower temperature than the subsequent step(s) and with the temperature being increased slowly in increments, e.g., per hour instead of per minute as in the quick start up. The gaseous mixture of $H_2$ and sulfur containing compound can be the same or different in the steps. In one embodiment, the first step is at about 100 to 375° C. (212° F. to 707° F.), preferably about 125 to 350° C. (257° F. to 662° F.), with a temperature ramp rate from 0.25 to 4° C. (0.45 to 7.2° F.) per hour. After the first step, temperature is held constant for a period of time from 2 to 24 hours, then ramped up for the second step at a rate from 5 to 20° C. (9 to 36° F.) per hour. In one embodiment, the second step is carried out at about 200 to 450° C. (392° F. to 842° F.), and preferably about 225 to 400° C. (437° F. to 752° F.).

In one embodiment, the sulfiding is done with elemental sulfur, wherein the sulfur is incorporated into the pores of the catalyst precursors. In this process, elemental sulfur is mixed with the catalyst precursor in an amount from 2 to 15 wt. % of the catalyst precursor weight, at a temperature below the melting point of sulfur. In one embodiment, the mixing is at 180 to 210° F. (82° to 99° C.). Sequentially or simultaneously with the mixing of precursor and elemental sulfur, the mixture is brought into contact with a high boiling organic liquid. The mixture is then heated to a temperature in the range of 250 to 390° F. (121° to 199° C.) in the presence of nitrogen, producing $H_2S$ and metal sulfides. In one embodiment, the organic liquid is selected from the group consisting of olefins, gasoline, white spirit, diesel, gas oils, mineral lube oils, and white oils.

In one embodiment, it is found that catalysts sulfided from embodiments of the catalyst precursors surprisingly give about the same 700° F.+ conversion rate whether sulfided via the gaseous phase, or in the liquid phase as a "quick" process. In one embodiment, it is found that the 700° F.+ conversion increases at least 25% with the use of catalysts sulfided in the liquid phase and via the "slow" process. In yet another embodiment, the 700° F.+ conversion doubles with a catalyst sulfided via the slow process.

In certain embodiments, the self-supported hydrotreating catalyst comprises nickel, molybdenum and tungsten. In certain embodiments, the self-supported hydrotreating catalyst comprises nickel, molybdenum, tungsten and titanium. In certain embodiments, the self-supported hydrotreating catalyst comprises nickel, molybdenum, tungsten and niobium. In certain embodiments, the self-supported hydrotreating catalyst comprises nickel, molybdenum, tungsten, niobium and titanium. In certain embodiments, the self-supported hydrotreating catalyst comprises nickel, molybdenum, tungsten, niobium and copper. In certain embodiments, the self-supported hydrotreating catalyst comprises nickel, molybdenum, tungsten and copper.

In certain embodiments, the self-supported hydrotreating catalyst comprises about 5 to about 9 wt % molybdenum, about 21 to 31 wt % nickel, and about 33 to about 42 wt % tungsten. In certain embodiments, the self-supported hydrotreating catalyst comprises about 5.9 to about 8.1 wt % molybdenum, about 21.8 to 30.7 wt % nickel, and about 34.4 to about 41.3 wt % tungsten.

A preferred catalyst precursor is the Ni—Mo—W maleate catalyst precursor. The catalyst is preferably sulfided with dimethyl sulfide (DMDS).

In certain embodiments, the self-supported hydrotreating catalyst is a catalyst comprising nickel, molybdenum and tungsten, for example ICR 1000, ICR 1001, ICR 1003 and ICR4000 (all available from Advanced Refining Technologies LLC).

In certain embodiments, the self-supported hydrotreating catalyst layer comprises or consists of one type of self-supported hydrotreating catalyst. In certain embodiments, the self-supported hydrotreating catalyst layer comprises or consists of two types of hydrocracking catalyst.

Hydrocarbon Feedstocks

A wide range of petroleum and chemical feedstocks can be hydroprocessed (or hydrotreated) by the layered catalyst reactor systems and processes. Suitable feedstocks include whole and reduced petroleum crudes, atmospheric and vacuum residua, propane deasphalted residua, e.g., brightstock, cycle oils, FCC tower bottoms, gas oils, including atmospheric and vacuum gas oils and coker gas oils, light to heavy distillates including raw virgin distillates, hydrockates, hydrotreated oils, dewaxed oils, slack waxes, Fischer-Tropsch waxes, raffinates, naphthas, and mixtures of these materials. Typical lighter feeds would include distillate fractions boiling approximately from about 175° C. (about 350° F.) to about 375° C. (about 750° F.). With feeds of this type a considerable amount of hydrocracked naphtha is produced which can be used as a low sulfur gasoline blend stock. Typical heavier feeds would include, for example, vacuum gas oils boiling up to about 593° C. (about 1100° F.) and usually in the range of about 350° C. to about 500° C. (about 660° F. to about 935° F.) and, in this case, the proportion of diesel fuel produced is correspondingly greater.

Processes for Hydrotreatment of Hydrocarbon Feedstocks

In one aspect, the present invention is directed to a process for hydrotreatment of hydrocarbon feedstocks comprising: (i) contacting a hydrocarbon feedstock which contains contaminants comprised of metals, sulfur, nitrogen and olefins with a layered catalyst reactor system as described herein in the presence of hydrogen to produce hydrocarbon product having a lower content of metals, sulfur, nitrogen and olefins than the hydrocarbon feedstock; (ii) passing the hydrocarbon feedstock sequentially through the layers of the layered catalyst reactor system vertically from top to bottom; and (iii) recovering the hydrocarbon product from the bottom of the layered catalyst reactor system. The process can be used to remove impurities or contaminants, such as metals, sulfur and nitrogen, and to saturate olefins and aromatic compounds, from the hydrocarbon feedstock. The process is carried out at conditions which facilitate the hydrodemetallization, hydrodesulfurization, and hydrodenitrification.

In an embodiment, the process is operated by conducting the feedstock, which contains high levels of sulfur and nitrogen, to the initial treating reaction stage to convert a substantial amount of the sulfur and nitrogen in the feed to inorganic form with a major objective in this step being a reduction of the feed nitrogen content. The hydrotreatment step is carried out in the exemplary layered catalyst reactor system in the presence of hydrogen. The conditions used are appropriate to hydrodesulfurization and/or denitrogenation depending on the feed characteristics. The product stream is then passed directly (without separation) or with separation and a water wash to the hydrocracking zone in which boiling range conversion is effected. The product stream from the first and second layers in the exemplary system together with hydrogen treat gas and other hydrotreating/hydrocracking reaction products including hydrogen sulfide and ammonia may pass to separators in which hydrogen, light ends, and inorganic nitrogen and hydrogen sulfide are removed from the hydrocracked liquid product stream. The recycle gas may be washed to remove ammonia and may be subjected to an amine scrub to remove hydrogen sulfide in order to improve the purity of the recycled hydrogen and so reduce product sulfur levels.

The product stream then proceeds to the hydrocracking and self-supported catalyst layers for processing. In certain embodiments, the removal of "hard sulfur" species, i.e., sulfur species having atmospheric boiling points in the range of about 93° C. to about 593° C. (200° F. to about 1100° F.), particularly in the range of about 350° C. to about 500° C. (about 660° F. to about 935° F.)

EXAMPLES

The disclosed embodiments are further illustrated by the following examples, which are not to be construed in any way as imposing limitation to the scope of this disclosure. Various other aspects, embodiments, modifications, and equivalents thereof may be apparent to one of ordinary skill in the art, after reading the description herein, without departing from the scope of the present disclosure.

Example 1

This study explores the hydrotreating of products derived from the LC Fining processes. Testing was done with LC Finate material based on Arab medium crude and with Urals based feeds.

Bench Scale Units (BSUs), Catalyst Systems, and Feeds

Several bench scale units were used for this study (BSUs 607, 612, and 911). Several catalyst systems were tested in separate runs in BSU607 (runs 56 to 62), BSU612 (runs 37 to 41), and BSU911 (runs 160 and 161).

The layered catalyst reactor systems used are described in Table 1. Whole extrudates shortened to an L/D of 1 to 2 and packed with -100 mesh alundum were used to prevent bypassing and channeling. One of the main targets of this study was the evaluation of ICR 1000/1001 performance in upgrading theses challenging feeds. Catalyst systems containing about 10% to about 20% ICR 1000 and/or about 14% to about 44% ICR 1001 were explored. Comparative examples included catalyst systems with ICR 183 and ICR 191 as hydrocracking catalysts. ICR 250 was used in conjunction with ICR 1000 and was typically positioned in front of (on top of) ICR 1000 or ICR1001. One comparative example included a catalyst system containing only ICR 250 (no ICR 1000 or ICR1001).

TABLE 1

| BSU | 607-56 | 612-37/38/39 | 607-57 | 911-160 | 911-161 | 612-40/41 | 59/60/61 | 607-62 |
|---|---|---|---|---|---|---|---|---|
| Top layer: Demet. Catalyst | ICR 132 (20%, 1.01 g, 9.88% LOI) | ICR 132 (20%, 1.01 g, 9.37% LOI) | ICR 132 (20%, 1.00 g, 10.1% LOI) | ICR 132 (20%, 1.04 g, 9.29% LOI) | ICR 132 (20%, 1.03 g, 9.90% LOI) | ICR 132 (20%, 1.01 g, 10.6% LOI) | ICR 132 (20%, 1.01 g, 10.29% LOI) | ICR 132 (20%, 1.01 g, 10.29% LOI) |
| Supported Hydrotreat. Catalyst | ICR 513 (48%, 3.87 g, 12.7% LOI) | ICR 513 (49%, 3.96 g, 12.7% LOI) | ICR 513 (32%, 2.53 g, 14.4% LOI) | ICR 513 (22%, 1.76 g, 14.8% LOI) | ICR 513 (22%, 1.78 g, 13.6% LOI) | ICR 513 (22%, 1.77 g, 14.3% LOI) | ICR 513 (22%, 1.79 g, 12.35% LOI) | ICR 513 (22%, 1.79 g, 12.35% LOI) |
| Hydrocrack. Catalyst | | | ICR 250 (10%, 0.80 g, 17.5% LOI) | ICR 250 (10%, 0.78 g, 17.2% LOI) | ICR 250 (10%, 0.79 g, 17.3% LOI) | ICR 250 (10%, 0.79 g, 18.2% LOI) | ICR 250 (10%, 0.77 g, 17.3% LOI) | ICR 250 (54%, 4.15 g, 17.3% LOI) |
| Self-supported Catalyst | | | ICR 1000 (10%, 1.35 g, 17.1% LOI) | ICR 1000 (20%, 2.71 g, 17.7% LOI) | ICR 1001 (14%, 1.65 g, 20.8% LOI) | ICR 1001 (14%, 1.68 g, 20.5% LOI) | ICR 1001 (44%, 5.20 g, 20.7% LOI) | |
| Hydrocrack. Catalyst | | | | | ICR 250 (10%, 0.79 g, 17.3% LOI) | ICR 250 (10%, 0.79 g, 18.2% LOI) | | |
| Self-supported Catalyst | ICR 183 (24%, 1.79 g, 6.79% LOI) | ICR 191 (24%, 1.72 g, 6.15% LOI) | ICR 183 (24%, 1.73 g, 8.24% LOI) | ICR 183 (24%, 1.76 g, 7.66% LOI) | ICR 1001 (20%, 2.36 g, 20.8% LOI) | ICR 1001 (20%, 2.40 g, 20.5% LOI) | | |
| Bottom layer: Supported Hydrotreat. Catalyst | ICR 513 (8%, 0.64 g, 12.7% LOI) | ICR 513 (8%, 0.66 g, 12.7% LOI) | ICR 513 (4%, 0.32 g, 14.4% LOI) | ICR 513 (4%, 0.32 g, 14.8% LOI) | ICR 513 (4%, 0.32 g, 13.6% LOI) | ICR 513 (4%, 0.32 g, 14.3% LOI) | ICR 513 (4%, 0.33 g, 12.4% LOI) | ICR 513 (4%, 0.32 g, 14.8% LOI) |

*LOI = loss on ignition.

The feeds used in most units were heavy vacuum gas oil (HVGO) from the LC Fining unit (ABQ160) and a 900–° F. VGO derived from this feed (ABQ1967). ABQ160 consists of 750% LC finate HVGO and 25% straight run (SR) HVGO. A blend of ABQ1560 with SRC HVGO to achieve a 50% blend of LC finer product with HVGO was used to evaluate dilution effects on activity/stability (TGQ9588). Additional feeds used were based on Ural derived feeds from RAM (Milazzo refinery LC Finer HVGO, TGQ9989) diluted with SRC HVGO to a 50/50 blend (CGQ0003) and Neste (Neste LC Finer Heavier VGO, ABQ1956) diluted with SRC HVGO to a 50/50 blend (CGQ197). Properties of the feeds used are shown in Table 2. Feed sample descriptions are provided below Table 2.

TABLE 2

| Feed ID | A | B | C | D | E | F | G | H |
|---|---|---|---|---|---|---|---|---|
| API Gravity | 15.8 | 16.5 | 21.7 | 17.7 | 19.0 | 20.0 | 19.1 | 20.6/20.0 |
| Sulfur, wppm | 16100 | 14680 | 22000 | 1.79 | 6286 | 14650 | 4370 | 13910/13340 |
| Nitrogen, wppm | 2500 | 2160 | 1000 | 1860 | 3000 | 1970 | 3470 | 2520/2520 |
| Carbon, wt. % | 86.7 | 86.6 | 85.5 | 86.4 | 87.4 | 86.7 | 87.4 | 86.4 |
| Hydrogen, wt. % | 11.5 | 11.7 | 12.3 | 11.6 | 11.7 | 11.9 | 11.8 | 11.9/12.0 |
| Aromatics, vol % | 53.2 | | 33.4 | 49.6 | 51.2 | 44.6 | 50.3 | 42.6/44.5 |
| Naphthenics, vol % | 26.1 | | 31.9 | 26.0 | 31.4 | 30.8 | 34.5 | 34.5/32.6 |
| Paraffins, vol % | 9.6 | | 15.7 | 12.2 | 10.9 | 14.1 | 10.0 | 13.3/13.9 |

TABLE 2-continued

| Feed ID | A | B | C | D | E | F | G | H |
|---|---|---|---|---|---|---|---|---|
| S comp., vol % | 11.2 | | 19.1 | 12.2 | 6.5 | 10.5 | 5.2 | 9.6/9.0 |
| PCI | 9530 | 5708 | 2249 | | | | 3860 | 2943/ |
| MCRT, wt. % | 1.13 | | 0.30 | 0.97 | | | 0.05 | |
| Viscosity 70° C., mPa · s | 49.3 | | | 36.6 | | | 22.2 | |
| UV, 226 nm (au/g/l) | 36.8 | | 26.5 | | | | 36.5 | 31.3/ |
| UV, 255 nm (au/g/l) | 30.6 | | 19.6 | | | | 24.7 | 21.0/ |
| UV, 272 nm (au/g/l) | 25.8 | | 15.5 | | | | 19.0 | 16.5/ |
| UV, 305 nm (au/g/l) | 12.1 | | 6.50 | | | | 7.73 | 6.76/ |
| UV, 310 nm (au/g/l) | 10.1 | | 5.40 | | | | 6.30 | 5.54/ |
| MW | 606 | 402 | 397 | 437 | 374 | 393 | 399 | 399 |
| SimDist., (wt. %-° F.) | | | | | | | | |
| 0.5/5 | 664/771 | 598/749 | 635/692 | 680/751 | 509/603 | 535/639 | 613/714 | 607/703 |
| 10/30 | 804/868 | 779/832 | 722/788 | 783/854 | 647/748 | 688/781 | 746/808 | 735/799 |
| 50/ | 912/ | 861/ | 838/ | 899/ | 817/ | 839/ | 849/ | 844/ |
| 70/90 | 959/1025 | 884/907 | 893/968 | 943/996 | 882/965 | 896/970 | 887/936 | 889/950 |
| 95/99.5 | 1053/1104 | 915/930 | 1002/1070 | 1014/1041 | 1000/1076 | 1001/1049 | 955/994 | 980/1037 |
| Wt. % <700° F. | 0.7 | 1.9 | 6.1 | 0.9 | 19.0 | 11.8 | 3.4 | 4.6/4.4 |
| Used in BSU run | 607-56/57/59, 911-160 | 612-39/41, 911-161, 607-61 | | 612-37 | | 612-38 | | 607-60, 612-40, 607-62 |

Feed Sample Descriptions:

A=ABQ1560=HVGO from GS Caltex LC Fining Unit (25% SR HVGO)

B=AB1967=LVGO 650-900 F from ABQ1560 GSC LC Finate

C=ABQ1214=SRC VGO Blend

D=TGQ9588=GSC LCF VGO 50/50 blend with SRC HVGO

E=TGQ9589=RAM LC Finate VGO

F=CGQ0003=RAM LC Finate VGO 50/50 blend with SRC HVGO

G=ABQ1956=Neste LC Finate Heavier VGO

H=GCGQ0107/520=Neste LC Finate VGO 50/50 blend with SRC HVGO

Catalyst Sulfiding

The catalyst systems were sulfided prior to use with VGO spiked with DMDS:

Reactor was heated to 250° F. and held for one hour under nitrogen flow (no feed flow, 200 mL·min$^{-1}$ nitrogen flow) at ambient pressure.

Changed to hydrogen at 321 mL·min$^{-1}$ flow rate and increased pressure to 800 psig.

Changed to sulfiding feed (2.5 wt % DMDS in diesel) at 13.45 g·h$^{-1}$ (LHSV=1.3 h$^{-1}$) and hydrogen rate to 255 mL·min$^{-1}$ (5500 SCF·bbl$^{-1}$ hydrogen) and held for 10 hours.

Raised reactor temperature to 482° F. at 30° F. h$^{-1}$ and held for 5 hours.

Raised reactor temperature to 572° F. at 30° F. h$^{-1}$ and held for 5 hours.

Raised reactor temperature to 650° F. at 30° F. h$^{-1}$ and held for 6 hours.

Changed to diesel ABQ0920 at a rate of 5.17 g. h$^{-1}$ (LHSV=0.5 h$^{-1}$), increased pressure to 2350 psig, decreased hydrogen flow rate to 89.07 ml·min$^{-1}$ (5000 scf·bbl$^{-1}$) and continued for 3 days to de-edge the catalyst.

Test Conditions

The process conditions for the run were:

0.40 h$^{-1}$ LHSV (0.50 h$^{-1}$ LHSV without demet catalyst ICR 132) and 0.8 h$^{-1}$ LHSV (1.0 h$^{-1}$ LHSV without demet catalyst ICR 132)

2350 psig total pressure (2250 psi inlet H$_2$ partial pressure)

8000 SCFB once through H$_2$

Reactor temperature was between 710° F. and 765° F. to achieve targets with different feeds.

Two strippers were used for units 607/612 with target cutpoint of 300° F. and 700° F.

One stripper was used for unit 911 with a target cutpoint of 700° F.

S was targeted to less than 100 ppm for the whole liquid product (WLP) and to less than 30 ppm in the diesel fraction for two stripper units (V3O sample).

N was targeted to less than 40 ppm in WLP.

All products (gas, STO, STB or V3O/V3B) were analyzed by SimDist for yield structure calculations.

The STB or V3O/V3B products were further analyzed for sulfur and nitrogen. For selected yield periods additional analyses were done.

These above conditions were chosen as initial test method with ABQ1560 which is considered a very difficult feed. The design information for a recent LC Max hydrotreater/hydrocracker (see EDP CLG Hydrocracking/Hydrotreating Technology Shandong Sincier Petrochemical Co Ltd, Vol 1, September 2014) shows different conditions, i.e:

Reactor inlet pressure of 2200 psi with an average hydrogen partial pressure of 2000 psi.

Inlet gas to oil ratio is less than 5000 SCF/bbl as compared to 8000 SCF/bbl in our initial test case.
LHSV is 0.7 $h^{-1}$ compared to 0.4/0.8 $h^{-1}$.
The feed is a blend with a ratio of 45 vol % LC finer product and 55 vol % SR HVGO.
The LC finer HVGO has a distillation EP of 952° F. (511° C.) with ~22% material boiling above 900° F.
The additional feeds described in Table 2 and used later during this study addressed this issue and brought the feed/reaction conditions closer to the Sincier design.
Feed conversions were generally done at two different conditions to estimate energies of activation for HCR/HDN/HDS and calculate normalized temperatures. Temperature normalization was generally targeted for 40 ppm nitrogen, 100 ppm sulfur and 30% hydrocracking into the 700-° F. fraction.

RESULTS AND DISCUSSION

Run conditions and test results for the finished runs in BSU607-56 to 61, BSU911-160 and 161, and 612-37 to 40 are shown in Tables 3, 4, 5 and 6 (the values shown are averaged over multiple 24 hour yield periods).

TABLE 3

Run Conditions and Test Results for Comparative Examples BSU-607-56, 605-57 and 911-160.

| BSU | 607-56 | | | 607-57 | | | 911-160 | | |
|---|---|---|---|---|---|---|---|---|---|
| Run Hours | 379-547 | 835-1003 | 1219-1339 | 432-552 | 864-936 | 1032-1080 | 793-865 | 1033-1057 | 1393-1441 |
| Catalyst System (Top to Bottom Layers) | | 20% ICR 132/ 48% ICR 513/ 24% ICR 183/ 8% ICR 513 | | | 20% ICR 132/ 32% ICR 513/ 10% ICR 250/ 10% ICR 1000/ 24% ICR 183/ 4% ICR 513 | | | 20% ICR 132/ 22% ICR 513/ 10% ICR 250/ 20% ICR 1000/ 24% ICR 183/ 4% ICR 513 | |
| Feed ID | | ABQ1560 | | | ABQ1560 | | | ABQ1560 | |
| Temp., ° F. | 745 | 755 | 765 | 735 | 745 | 755 | 726 | 736 | 751 |
| WHSV, $h^{-1}$ | 0.54 | 0.54 | 0.54 | 0.49 | 0.49 | 0.49 | 0.46 | 0.46 | 0.46 |
| LHSV, $h^{-1}$ | 0.41 | 0.41 | 0.41 | 0.39 | 0.39 | 0.39 | 0.40 | 0.40 | 0.40 |
| Tot. P, psig | 2350 | 2350 | 2350 | 2350 | 2350 | 2350 | 2360 | 2350 | 2340 |
| Inlet $H_2$ P, psia | 2300 | 2300 | 2300 | 2300 | 2300 | 2300 | 2310 | 2310 | 2300 |
| Gas Rate, SCFB | 7730 | 7710 | 7710 | 8000 | 8010 | 8000 | 7830 | 7830 | 7830 |
| Conv <700° F., wt. % | 21.5 | 32.5 | 49.1 | 20.4 | 31.6 | 48.2 | 12.8 | 20.3 | 44.9 |
| HCR k, $h^{-1}$ | 0.13 | 0.21 | 0.37 | 0.11 | 0.19 | 0.32 | 0.06 | 0.11 | 0.27 |
| No loss yields, wt. % | | | | | | | | | |
| Methane | 0.19 | 0.25 | 0.31 | 0.16 | 0.21 | 0.27 | 0.11 | 0.14 | 0.23 |
| Ethane | 0.23 | 0.32 | 0.38 | 0.2 | 0.29 | 0.34 | 0.15 | 0.19 | 0.32 |
| Propane | 0.32 | 0.47 | 0.66 | 0.27 | 0.51 | 0.71 | 0.2 | 0.27 | 0.66 |
| i-Butane | 0.05 | 0.14 | 0.48 | 0.05 | 0.115 | 0.52 | 0.03 | 0.07 | 0.42 |
| n-Butane | 0.29 | 0.42 | 0.82 | 0.25 | 0.44 | 0.83 | 0.15 | 0.26 | 0.74 |
| C5-180° F. | 1.56 | 2.55 | 5.05 | 1.61 | 2.57 | 3.97 | 0.59 | 1.11 | 3.42 |
| 180-250° F. | 0.28 | 0.97 | 3.43 | 0.24 | 0.94 | 3.15 | 0.18 | 0.5 | 2.96 |
| 250-550° F. | 8.02 | 14.8 | 25.4 | 7.29 | 14.3 | 25.8 | 3.94 | 7.35 | 23.2 |
| 550-700° F. | 11 | 12.8 | 13 | 10.8 | 12.6 | 13.1 | 7.74 | 10.9 | 13.4 |
| 700° F.+ | 77.4 | 66.9 | 50.6 | 78.5 | 67.6 | 51.4 | 86 | 78.7 | 54.6 |
| C5+ | 98.3 | 98 | 97.5 | 98.4 | 98 | 97.4 | 98.4 | 98.5 | 97.5 |
| Mass Closure, wt. % | 97.8 | 97.9 | 98.1 | 98.5 | 99.2 | 99 | 99 | 99 | 96.1 |
| Chem $H_2$ Cons, SCFB | 1070 | 1230 | 1430 | 1020 | 1260 | | 840 | 1010 | 1370 |
| WLP S, ppm | 68.4 | 37 | 24.2 | 84.4 | 46.4 | 21.1 | 247 | 91.2 | 30 |
| WLP N, ppm | 58.2 | 25.8 | 11.4 | 55.3 | 24.8 | 5.2 | 170 | 54.9 | 8.7 |
| V3O Inspection Results: | | | | | | | STO (stripper overhead product) | STO | STO |
| S, ppm | 12.7 | 6.2 | <5 | 11.4 | 6.4 | <5 | 49.4 | 25.1 | 16.2 |
| N, ppm | 8.8 | 2.3 | 0.73 | 5.7 | 1.3 | <0.3 | 67 | 2.5 | <0.3 |
| API Gravity | 26.7 | 29.4 | 33.6 | 26.8 | 29.2 | 33.4 | | 30.8 | 36.9 |
| H (NMR), wt. % | 12.6 | 12.9 | 13.1 | 12.6 | 12.9 | | | | |
| V3B Inspection Results: | | | | | | | STB (stripper bottoms product) | STB | STB |
| N, ppm | 72.1 | 36.6 | 20.7 | 66.4 | 34.5 | 9.7 | 185 | 63.5 | 14 |
| S, ppm | 84.2 | 51.1 | 41.4 | 101 | 64 | 36.1 | 269 | 106 | 48.5 |

TABLE 3-continued

Run Conditions and Test Results for Comparative Examples BSU-607-56, 605-57 and 911-160.

| BSU | 607-56 | | | 607-57 | | | 911-160 | | |
|---|---|---|---|---|---|---|---|---|---|
| H (NMR), wt. % | 13.1 | 13.2 | 13.4 | 13 | 13.3 | | 12.7 | 12.9 | 13.3 |
| Stripper Perf. | | | | | | | | | |
| S1 Wt. % Overlap | 0.3 | 0.7 | 1.8 | 0.3 | 0.8 | 1.6 | 0.5 | 1 | 1.3 |
| S1 ASL Cut Pt., ° F. | 342 | 336 | 327 | 333 | 333 | 330 | 655 | 645 | 660 |
| S1 Btm Temp., ° F. | 200 | 200 | 200 | 200 | 200 | 200 | 650 | 651 | 650 |
| S2 Wt. % Overlap | 2.7 | 2.4 | 2 | 2 | 2.3 | 1.7 | | | |
| S2 Cut Pt., ° F. | 714 | 713 | 706 | 694 | 699 | 711 | | | |
| S2 Btm Temp, ° F. | 550 | 540 | 520 | 520 | 520 | 520 | | | |

TABLE 4

Run Conditions and Test Results for Comparative Examples BSU-607-59 and 612-37.

| BSU | 607-59 | | | 612-37 | | | |
|---|---|---|---|---|---|---|---|
| Run Hours | 212-332 | 572-668 | 716-836 | 405-501 | 837-885 | 1221-1341 | 1725-1773 |
| Catalyst System (Top to Bottom Layers) | 20% ICR 132/22% ICR 513/10% ICR 250/44% ICR 1001/4% ICR 513 | | | 20% ICR 132/48% ICR 513/24% ICR 191/8% ICR 513 | | | |
| Feed ID | ABQ1560 | | | TGQ9588 | | | |
| Temp., ° F. | 716 | 731 | 736 | 730 | 740 | 740 | 740 |
| WHSV, h$^{-1}$ | 0.42 | 0.41 | 0.41 | 0.53 | 0.52 | 1.1 | 1.06 |
| LHSV, h$^{-1}$ | 0.4 | 0.39 | 0.39 | 0.4 | 0.4 | 0.81 | 0.81 |
| Tot. P, psig | 2350 | 2350 | 2350 | 2350 | 2350 | 2350 | 2350 |
| Inlet H$_2$ P, psia | 2300 | 2302 | 2302 | 2280 | 2280 | 2280 | 2280 |
| Gas Rate, SCFB | 7620 | 7693 | 7685 | 7770 | 8150 | 7730 | 7730 |
| Conv <700° F., wt. % | 12.4 | 19 | 20.9 | 18.3 | 32.3 | 13.4 | 21.4 |
| HCR k, h$^{-1}$ | 0.06 | 0.09 | 0.1 | 0.5 | 0.2 | 0.15 | 0.25 |
| No loss yields, wt. % | | | | | | | |
| Methane | 0.09 | 0.16 | 0.18 | 0.11 | 0.16 | 0.09 | 0.15 |
| Ethane | 0.11 | 0.19 | 0.23 | 0.15 | 0.21 | 0.11 | 0.2 |
| Propane | 0.14 | 0.26 | 0.35 | 0.21 | 0.39 | 0.14 | 0.3 |
| i-Butane | 0.02 | 0.04 | 0.06 | 0.03 | 0.18 | 0.02 | 0.05 |
| n-Butane | 0.12 | 0.22 | 0.4 | 0.19 | 0.41 | 0.09 | 0.23 |
| C5-180° F. | 0.61 | 1.33 | 1.28 | 0.9 | 2.27 | 0.51 | 0.93 |
| 180-250° F. | 0.07 | 0.19 | 0.3 | 0.19 | 1.26 | 0.11 | 0.42 |
| 250-550° F. | 3.64 | 6.5 | 7.38 | 5.36 | 14 | 3.5 | 7.38 |
| 550-700° F. | 7.86 | 10.3 | 11 | 11.6 | 14 | 9.39 | 12.3 |
| 700° F.+ | 86.4 | 80 | 78.2 | 80.3 | 66.8 | 85 | 77.2 |
| C5+ | 98.6 | 98.3 | 98.2 | 98.3 | 98.4 | 98.5 | 98.2 |
| Mass Closure, wt. % | 99.4 | 98.8 | 99.2 | 97.7 | 95.8 | 98.6 | 98.5 |
| Chem H$_2$ Cons, SCFB | 930 | 1100 | 1168 | | 1300 | 746 | 890 |
| WLP S, ppm | 147 | 35.2 | 28.8 | 69.7 | 21.4 | 402 | 116 |
| WLP N, ppm | 92.6 | 16.1 | 14.2 | 50.4 | 6.3 | 214 | 73 |
| V3O Inspection Results: | | | | | | | |
| S, ppm | 40.8 | 9.71 | 7.72 | 5.1 | <5 | 46.8 | 7.7 |
| N, ppm | 34.2 | 3.06 | 2.31 | 2.7 | <0.3 | 95.1 | 3.9 |
| API Gravity | 22.8 | 25.7 | 26.2 | | 30.4 | 27.9 | 29.5 |
| H (NMR), wt. % | 12.4 | 12.7 | 12.7 | | 13 | 12.4 | 12.5 |
| V3B Inspection Results: | | | | | | | |
| N, ppm | 106 | 23.9 | 19 | 56.3 | 8.8 | 434 | 84.1 |
| S, ppm | 172 | 44.8 | 35.7 | 77.8 | 28.7 | 225 | 133 |
| H (NMR), wt. % | 13 | 13.1 | 13.2 | | 13.5 | 12.8 | 12.9 |
| Stripper Perf. | | | | | | | |
| S1 wt. % Overlap | 0.3 | 0.3 | 0.4 | 0.3 | 0.6 | 0.2 | 0.4 |
| S1 ASL Cut Pt., ° F. | 389 | 341 | 342 | 374 | 363 | 337 | 331 |
| S1 Btm Temp, ° F. | 250 | 200 | 200 | 200 | 200 | 200 | 200 |
| S2 Wt. % Overlap | 2.7 | 2.1 | 2.2 | 0.9 | 1.1 | 1 | 1.2 |
| S2 Cut Pt., ° F. | 759 | 721 | 718 | 641 | 689 | 654 | 635 |
| S2 Btm Temp, ° F. | 600 | 550 | 550 | 520 | 600 | 600 | 600 |

TABLE 5

Run Conditions and Test Results for Comparative Examples BSU-612-39 and 607-61 and Exemplary Example 911-161.

| BSU | 612-39 | | | 911-161 | | 607-61 | |
|---|---|---|---|---|---|---|---|
| Run Hours | 2877-2925 | 3093-3189 | 3261-3357 | 194-242 | 362-410 | 2372-2420 | 2756-2852 |
| Catalyst System (Top to Bottom Layers) | 20% ICR 132/48% ICR 513/24% ICR 191/8% ICR 513 | | | 20% ICR 132/22% ICR 513/10% ICR 250/14% ICR 1001/10% ICR 250/20% ICR 1001/4% ICR 513 | | 20% ICR 132/22% ICR 513/10% ICR 250/44% ICR 1001/4% ICR 513 | |

TABLE 5-continued

Run Conditions and Test Results for Comparative Examples BSU-612-39 and 607-61 and Exemplary Example 911-161.

| BSU | 612-39 | | 911-161 | | 607-61 | |
|---|---|---|---|---|---|---|
| Feed ID | ABQ1967 | | ABQ1967 | | ABQ1967 | |
| Temp., °F. | 740 | 740 | 750 | 736 | 736 | 737 | 732 |
| WHSV ($h^{-1}$) | 0.51 | 1.05 | 1.04 | 0.44 | 0.88 | 0.42 | 0.42 |
| LHSV, $h^{-1}$ | 0.39 | 0.8 | 0.79 | 0.4 | 0.8 | 0.4 | 0.4 |
| Tot. P, psig | 2350 | 2350 | 2350 | 2318 | 2327 | 2350 | 2350 |
| Inlet $H_2$ P, psia | 2275 | 2273 | 2274 | 2244 | 2253 | 2269 | 2269 |
| Gas Rate, SCFB | 7994 | 7831 | 7931 | 7958 | 8040 | 7512 | 7519 |
| Conv <700° F., wt. % | 37.7 | 14.7 | 18.0 | 32.0 | 17.3 | 27.7 | 23.8 |
| HCR k, $h^{-1}$ | 0.24 | 0.17 | 0.21 | 0.17 | 0.16 | 0.14 | 0.11 |
| No loss yields, wt. % | | | | | | | |
| Methane | 0.18 | 0.09 | 0.12 | 0.02 | 0.1 | 0.18 | 0.13 |
| Ethane | 0.28 | 0.13 | 0.17 | 0.25 | 0.13 | 0.24 | 0.17 |
| Propane | 0.54 | 0.16 | 0.23 | 0.38 | 0.18 | 0.36 | 0.22 |
| i-Butane | 0.21 | 0.02 | 0.04 | 0.06 | 0.02 | 0.07 | 0.03 |
| n-Butane | 0.5 | 0.14 | 0.21 | 0.37 | 0.15 | 0.33 | 0.21 |
| C5-180° F. | 2.06 | 0.55 | 0.66 | 1.5 | 0.56 | 1.22 | 1.01 |
| 180-250° F. | 1.59 | 0.12 | 0.2 | 0.86 | 0.28 | 0.69 | 0.41 |
| 250-550° F. | 16.6 | 3.71 | 5.22 | 11.4 | 4.57 | 9.31 | 7.53 |
| 550-700° F. | 16.8 | 11.3 | 12.6 | 18.3 | 12.6 | 16.5 | 15.3 |
| 700° F.+ | 61.1 | 82.9 | 79.9 | 66.4 | 80.7 | 70.7 | 74.4 |
| C5+ | 98.2 | 98.6 | 98.5 | 98.4 | 98.7 | 98.5 | 98.7 |
| Mass Closure, wt. % | 98.2 | 98.6 | 98.5 | 97.4 | 98 | 99.8 | 98.2 |
| Chem $H_2$ Cons SCFB | 1142 | 559 | 639 | | | 1081 | 999 |
| WLP S, ppm | 24 | 356 | 169 | 8.2 | 120 | 15.4 | 25.3 |
| WLP N, ppm | 5.8 | 228 | 146 | 1.1 | 92.4 | 5.9 | 14 |
| V3O Inspection Results: | | | | STO | STO | | |
| :S, ppm | <0.5 | 33 | | 18 | 50 | <5 | <5 |
| N, ppm | <0.3 | 111 | 33 | <0.3 | 12 | 1.5 | 3.4 |
| API Gravity | 29 | 26.5 | 27.2 | 34.1 | 32.1 | 25.2 | 24.4 |
| H (NMR), wt. % | 12.8 | 12.2 | 12.3 | | | 12.8 | 12.6 |
| V3B Inspection Results: | | | | STB | STB | | |
| N, ppm | 8.3 | 239 | 160 | 1.3 | 100 | 8.1 | 18.4 |
| S, ppm | 33 | 379 | 188 | 10 | 129 | 20.8 | 34.1 |
| H (NMR), wt. % | 13.3 | 12.5 | 12.6 | 13.4 | 12.7 | 13.3 | 13.3 |
| Stripper Perf. | | | | | | | |
| S1 Wt. % Overlap | 1.1 | 0.2 | 0.3 | 1.3 | 0.6 | 0.7 | 0.5 |
| S1 ASL Cut Pt., °F. | 371 | 337 | 339 | 604 | 606 | 376 | 380 |
| S1 Btm Temp, °F. | 200 | 200 | 200 | 600 | 600 | 250 | 250 |
| S2 Wt. % Overlap | 1.5 | 1.3 | 1.4 | | | 3 | 3.2 |
| S2 Cut Pt., °F. | 662 | 652 | 648 | | | 728 | 727 |
| S2 Btm Temp, °F. | 600 | 600 | 600 | | | 600 | 600 |

TABLE 6

Run Conditions and Test Results for Comparative Examples BSU-612-38 and 607-60 and Exemplary Example 612-40.

| BSU | 612-38 | | 607-60 | | 612-40 | |
|---|---|---|---|---|---|---|
| Run Hours | | | | | | |
| Catalyst System (Top to Bottom Layers) | 20% ICR 132/ 48% ICR 513/ 24% ICR 191/ 8% ICR 513 | | 20% ICR 132/ 22% ICR 513/ 10% ICR 250/ 44% ICR 1001/ 4% ICR 513 | | 20% ICR 132/ 22% ICR 513/ 10% ICR 250/ 14% ICR 1001/ 10% ICR 250 20% ICR 1001/ 4% ICR 513 | |
| Feed ID | CGQ0003 | | CGQ0107 | | CGQ0107 | |
| Temp., °F. | 740 | 750 | 731 | 736 | 731 | 726 |
| WHSV, $h^{-1}$ | 1.04 | 1.03 | 0.72 | 0.72 | 0.74 | 0.74 |
| LHSV, $h^{-1}$ | 0.81 | 0.81 | 0.7 | 0.7 | 0.7 | 0.7 |
| Tot. P, psig | 2350 | 2350 | 2350 | 2350 | 2350 | 2350 |
| Inlet $H_2$ P, psia | 2270 | 2273 | 2273 | 2273 | 2275 | 2275 |
| Gas Rate, SCFB | 7754 | 7765 | 7674 | 7695 | 7805 | 7837 |
| Conv <700° F., wt. % | 15.0 | 19.7 | 17.1 | 20.4 | 20.6 | 15.8 |
| HCR k, $h^{-1}$ | 0.17 | 0.22 | 0.13 | 0.16 | 0.17 | 0.13 |
| No loss yields, wt. % | | | | | | |
| Methane | 0.13 | 0.13 | 0.11 | 0.13 | 0.11 | 0.09 |
| Ethane | 0.16 | 0.16 | 0.13 | 0.14 | 0.14 | 0.1 |
| Propane | 0.24 | 0.21 | 0.21 | 0.2 | 0.2 | 0.14 |
| i-Butane | 0.04 | 0.04 | 0.03 | 0.04 | 0.04 | 0.03 |
| n-Butane | 0.17 | 0.18 | 0.15 | 0.19 | 0.17 | 0.12 |
| C5-180° F. | 0.76 | 1.16 | 0.72 | 0.75 | 0.65 | 0.54 |
| 180-250° F. | 0.03 | 0.07 | 0.23 | 0.32 | 0.48 | 0.21 |
| 250-550° F. | 5.09 | 7.71 | 5.74 | 7.5 | 7.36 | 5.01 |
| 550-700° F. | 18.1 | 19.3 | 13.5 | 14.6 | 14.9 | 13 |
| 700° F.+ | 74.5 | 70.5 | 78.6 | 75.7 | 75.3 | 80 |

TABLE 6-continued

Run Conditions and Test Results for Comparative Examples
BSU-612-38 and 607-60 and Exemplary Example 612-40.

| BSU | 612-38 | | 607-60 | | 612-40 | |
|---|---|---|---|---|---|---|
| C5+ | 98.5 | 98.7 | 98.8 | 98.8 | 98.7 | 98.9 |
| Mass Closure, wt. % | 98.3 | 98.4 | 99 | 97.5 | 98.6 | 98.6 |
| Chem H$_2$ Cons SCFB | 660 | 793 | 866 | 1003 | | |
| WLP S, ppm | 125 | 47.4 | 31 | 14.6 | 14.7 | 44.7 |
| WLP N, ppm | 101 | 32.3 | 20.8 | 8.6 | 6.8 | 32.5 |
| V3O Inspection Results: | | | | | | |
| S, ppm | 10.4 | <5 | 9.5 | <5 | <5 | 7.03 |
| N, ppm | 36.7 | 1.78 | 4.9 | 1.7 | <0.3 | 5.54 |
| API Gravity | 28.4 | 29.3 | 27.3 | 28 | 28.5 | 27.6 |
| H (NMR), wt. % | 12.6 | 12.7 | 12.9 | 13 | | |
| V3B Inspection Results: | | | | | | |
| N, ppm | 109 | 38 | 28.1 | 11 | 7.88 | 36 |
| S, ppm | 140 | 54.5 | 37.6 | 17.9 | 16.5 | 50 |
| H (NMR), wt. % | 13 | 13.2 | 13.3 | 13.5 | | |
| Stripper Perf. | | | | | | |
| S1 Wt. % Overlap | 0.2 | 0.3 | 0.3 | 0.4 | 0.6 | 0.4 |
| S1 ASL Cut Pt., ° F. | 328 | 334 | 357 | 351 | 382 | 393 |
| S1 Btm Temp, ° F. | 200 | 200 | 250 | 250 | 250 | 250 |
| S2 Wt. % Overlap | 1.8 | 1.7 | 2.9 | 2.9 | 1.2 | 1.1 |
| S2 Cut Pt., ° F. | 633 | 626 | 717 | 712 | 639 | 648 |
| S2 Btm Temp, ° F. | 600 | 600 | 600 | 600 | 600 | 600 |

Normalized temperatures for hydrocracking to the <700° F. fraction (HCR <700° F., 300%), hydrodenitrogenation (HDN, 40 ppm), and hydrodesulfurization (HIDS, 100 ppm) are shown in FIGS. 1 to 10 together with actual reactor temperatures and calculated energies of activation.

Figure 3:
FIG. 3 graphically depicts normalized temperatures for hydrotreatment processes with a comparative layered catalyst reactor system (one hydrocracking catalyst layer and one self-supported hydrotreating catalyst layer; BSU911-160).
Figure 4:
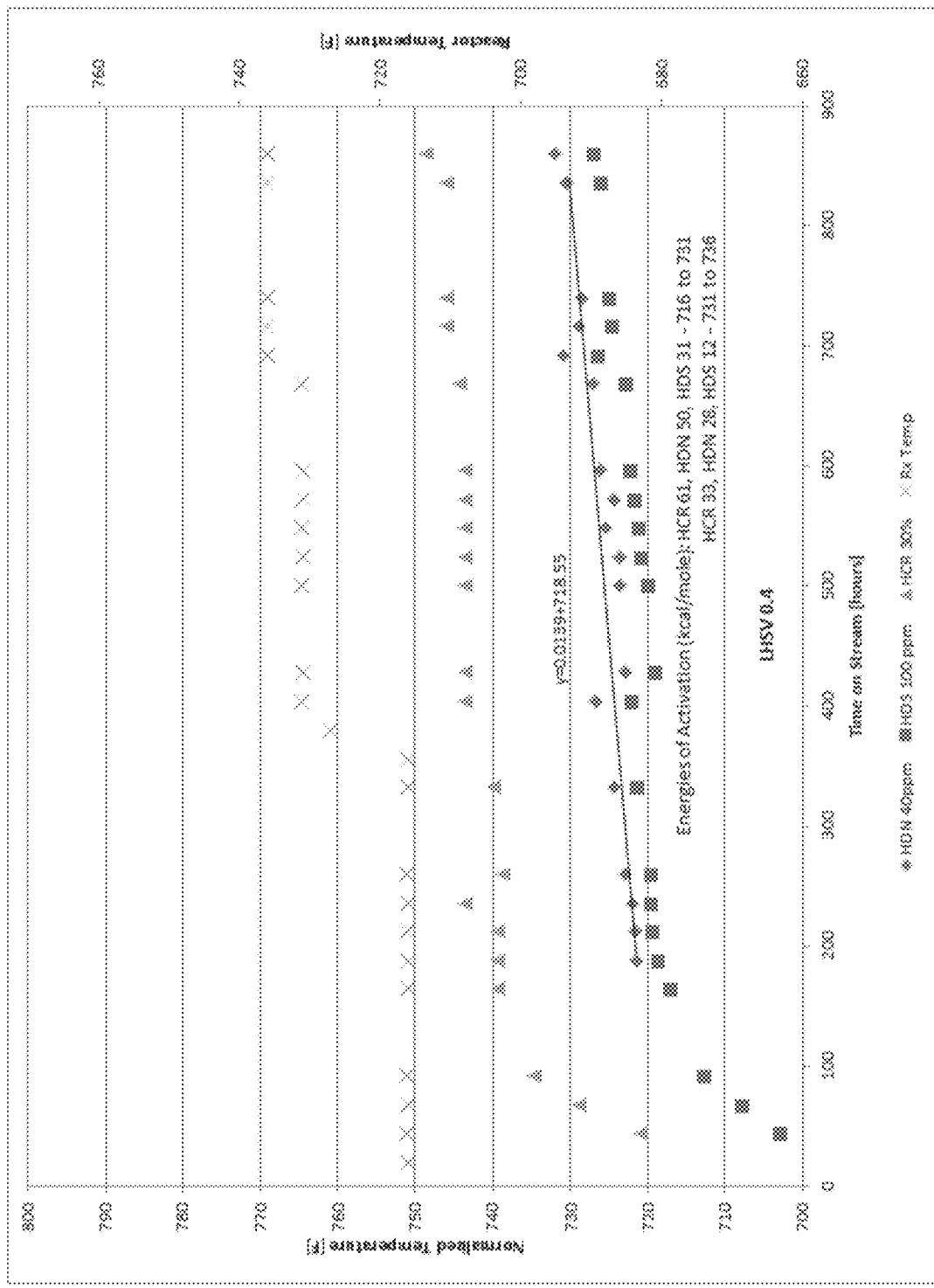
FIG. 4 graphically depicts normalized temperatures for hydrotreatment processes with a comparative layered catalyst reactor system (one hydrocracking catalyst layer and one self-supported hydrotreating catalyst layer; BSU607-59).
Figure 5:
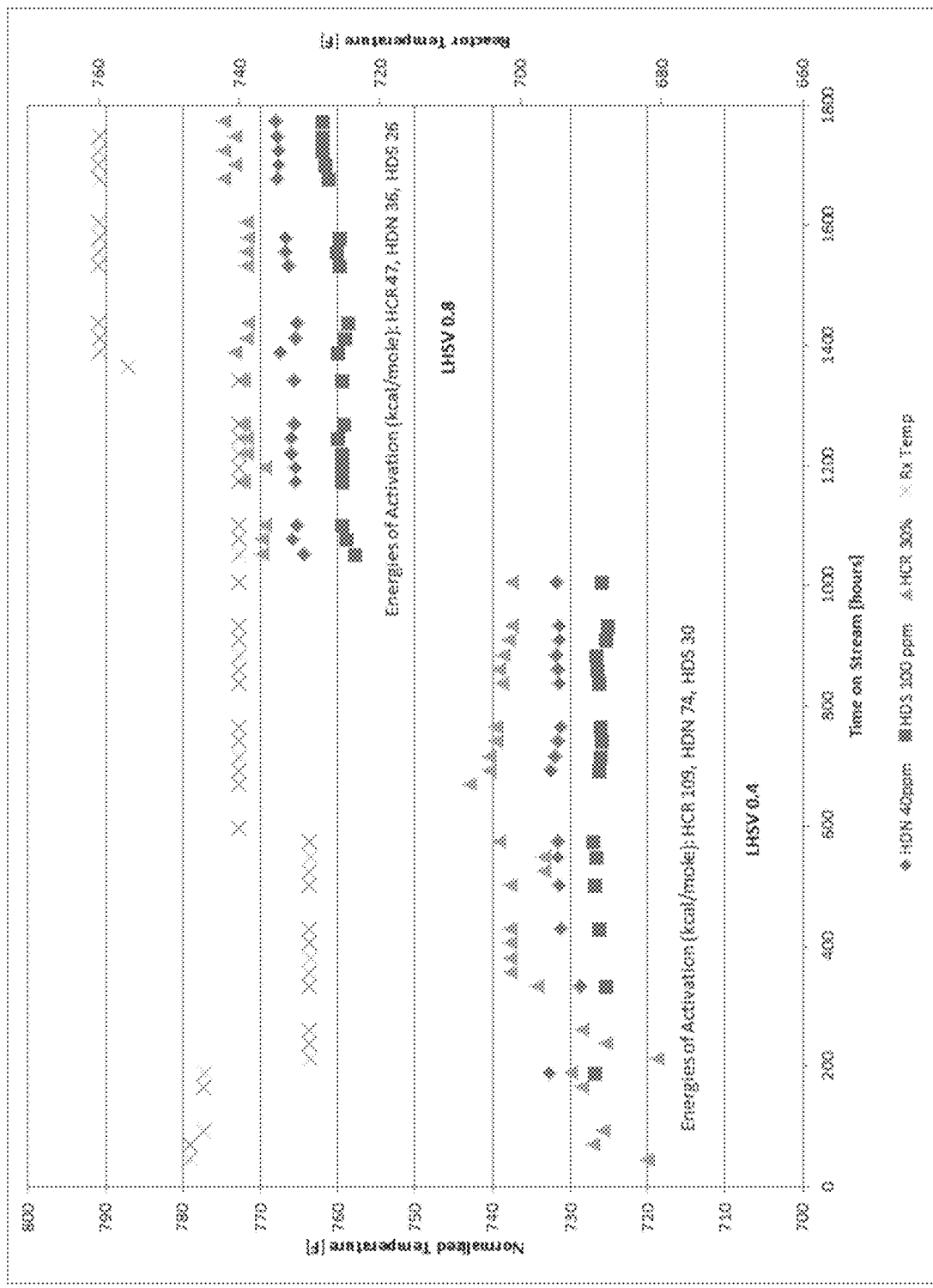
FIG. 5 graphically depicts normalized temperatures for hydrotreatment processes with a comparative layered catalyst reactor system (no hydrocracking or self-supported hydrotreating catalyst layers; BSU 612-37).
Figure 6:
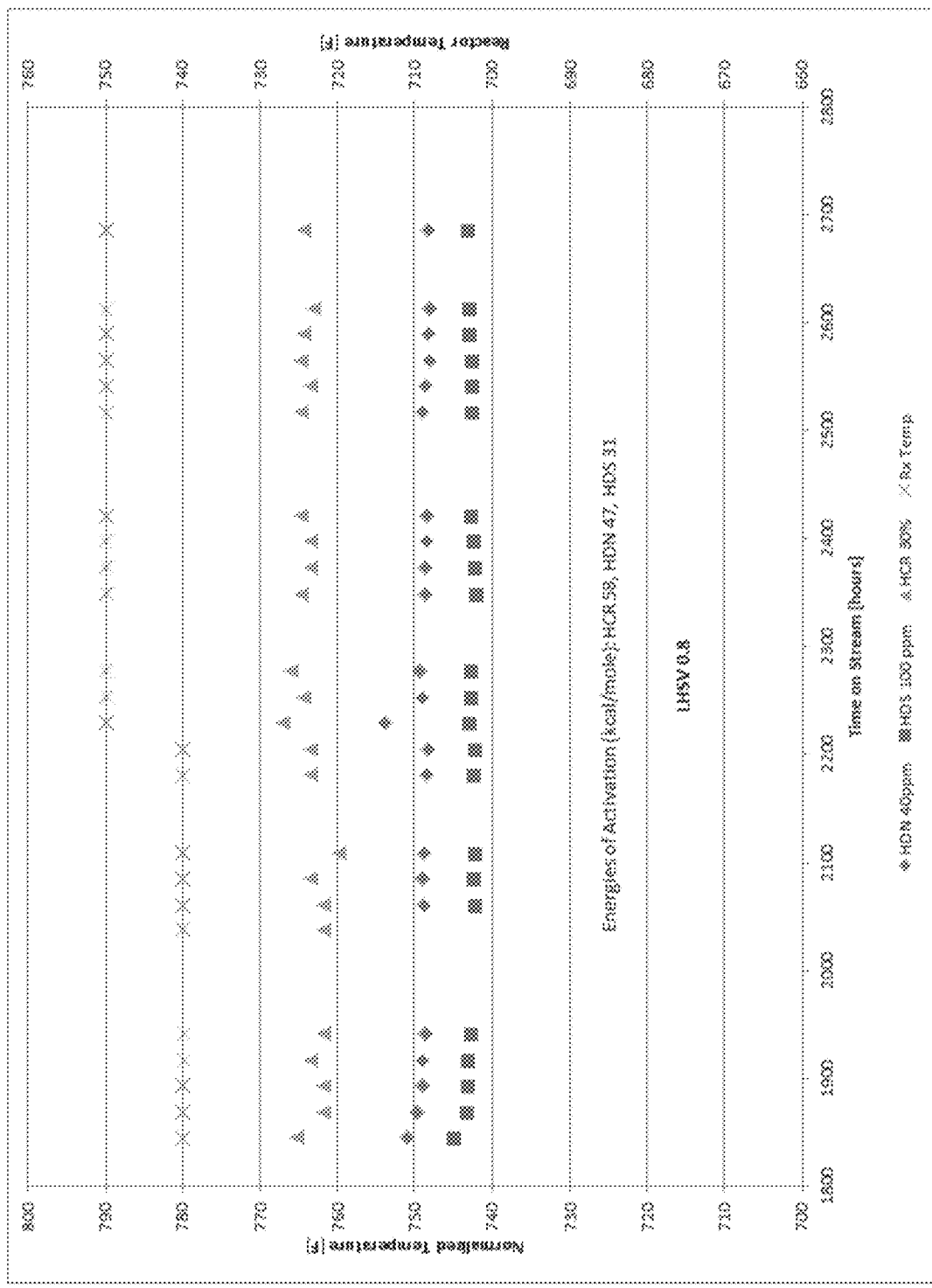
FIG. 6 graphically depicts normalized temperatures for hydrotreatment processes with a comparative layered catalyst reactor system (no hydrocracking or self-supported hydrotreating catalyst layers; BSU 612-38).
Figure 7:
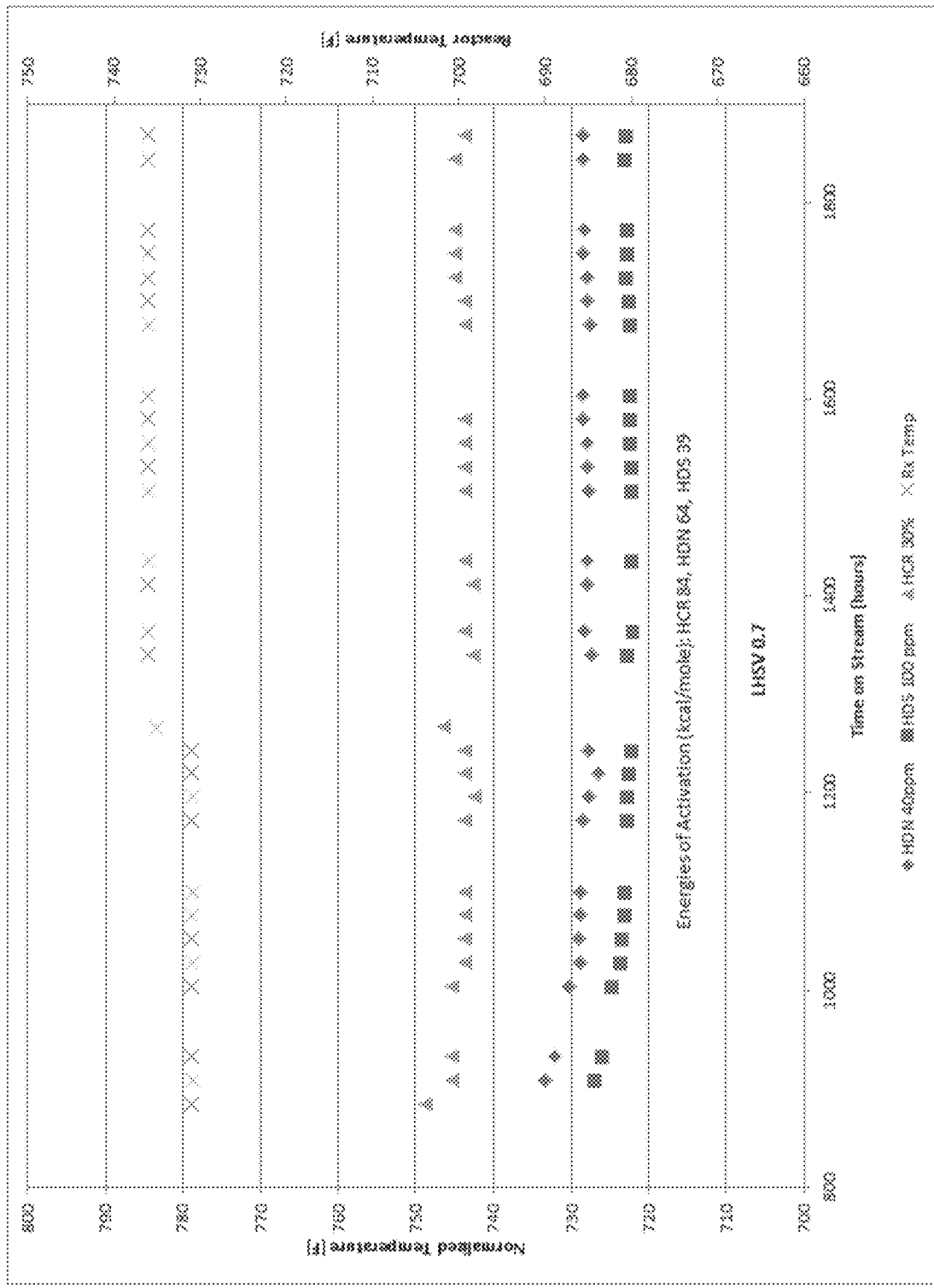
FIG. 7 graphically depicts normalized temperatures for hydrotreatment processes with a comparative layered catalyst reactor system (one hydrocracking catalyst layer and one self-supported hydrotreating catalyst layer; BSU607-60).
Figure 8:
FIG. 8 graphically depicts normalized temperatures for hydrotreatment processes with an exemplary layered catalyst reactor system (two hydrocracking catalyst layers and two self-supported hydrotreating catalyst layers; BSU612-40).
Figure 9:
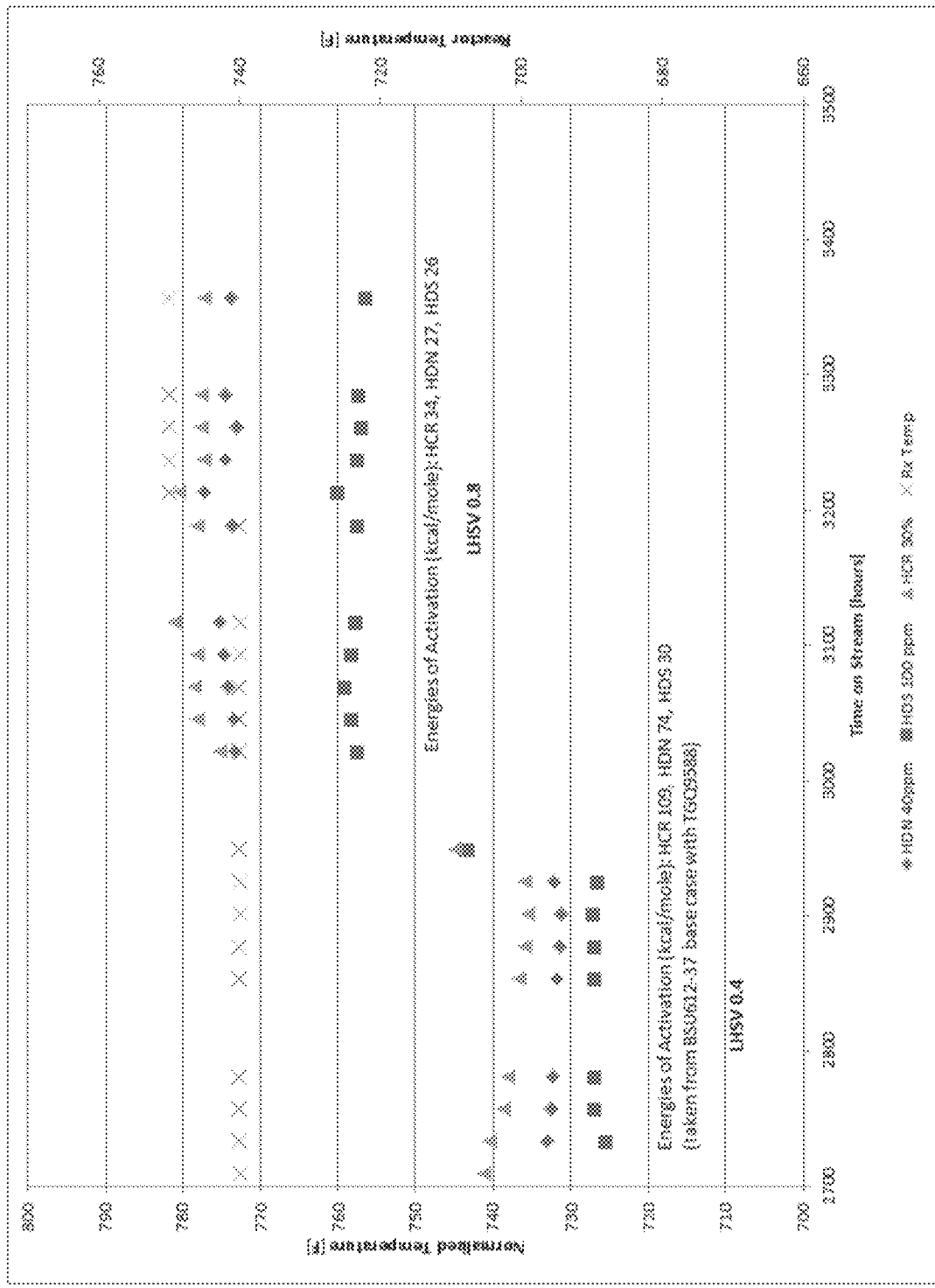
FIG. 9 graphically depicts normalized temperatures for hydrotreatment processes with a comparative layered catalyst reactor system (no hydrocracking or self-supported hydrotreating catalyst layers; BSU612-39).
Figure 10:
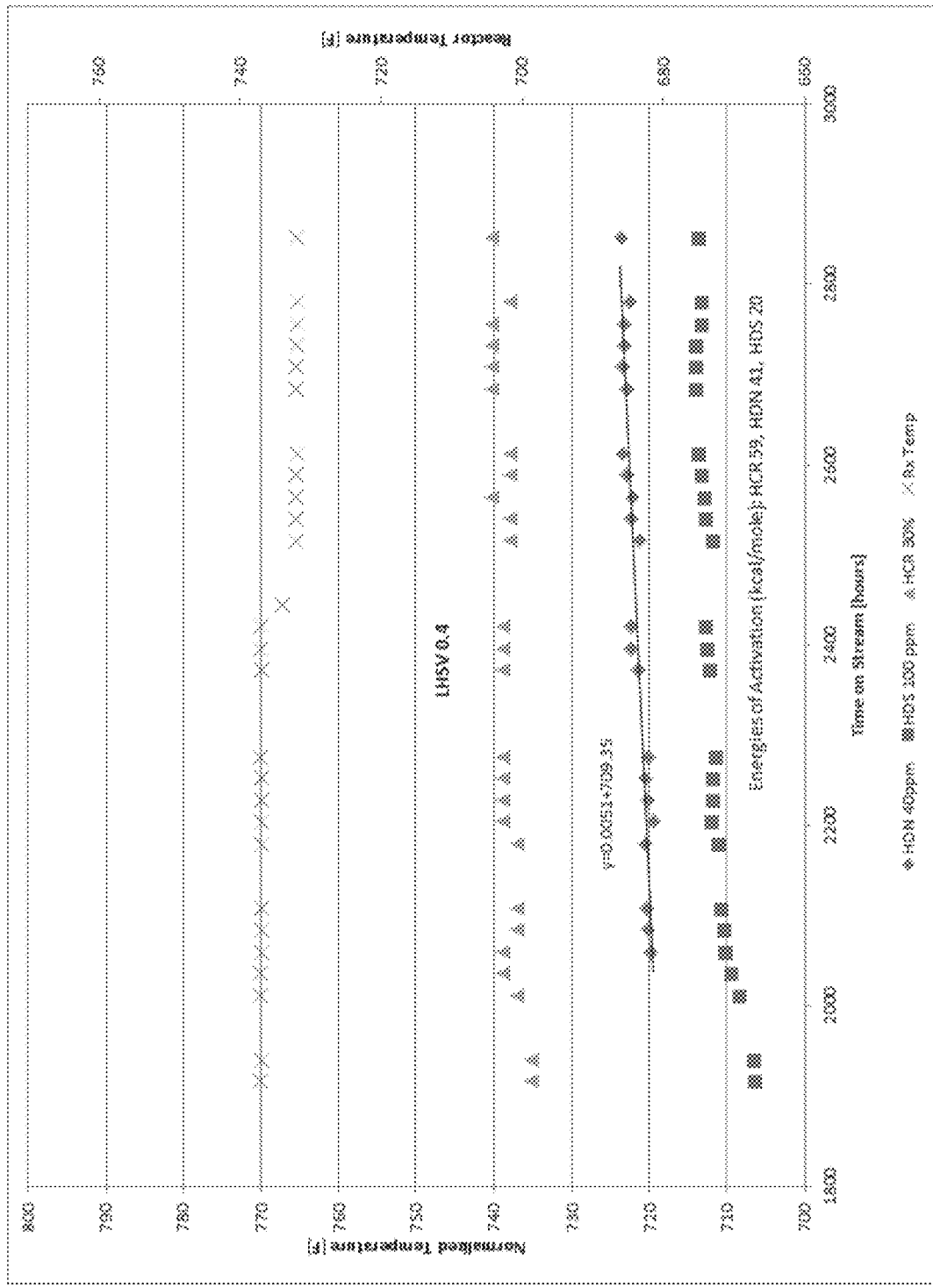
FIG. 10 graphically depicts normalized temperatures for hydrotreatment processes with a comparative layered catalyst reactor system (one hydrocracking catalyst layer and one self-supported hydrotreating catalyst layer; BSU607-61).

For the heaviest feed, ABQ1560, with a large amount boiling >900° F. stable operation could not be achieved with any catalyst system. While base case (no ICR 1000) and 10% ICR 250/10% ICR 1000 showed high deactivation in the range of 10° F./1000 hours (FIGS. 1 and 2), the catalysts system with 10% ICR 250/20% ICR 1000 showed an increased stability (~4° F./1000 hours, FIG. 3), which was lost when the ICR 1000 content was increased to 44% (FIG. 4). Compared to the base case, the activity advantage of using ICR 1000 can be as high as 20° F. In FIG. 3, the jump in normalized temperature at around 400 h time-on-stream was due to a previous feed loss for more than 36 hours which incurred an activity penalty after restart.

Diluting ABQ1560 (75/25 blend of full range LC Finate VGO and SR HVGO) to a 50/50 blend of LC Finate and SR HVGO (TGQ9588) gave a stable run for the base case with ICR 191 (which is considered to have the same activity as ICR 183) for both HDN and HDS. At a low LHSV of 0.4 h$^{-1}$ the required temperature for 40 ppm N and 100 ppm S was between 720 and 730° F., but increased by more than 30° F. with a higher LHSV of 0.8 (FIG. 5), which would be closer to the required space velocity for converting this feed.

Testing a 50/50 blend of RAM LC Finate with SR HVGO, i.e. CGQ0003, at a LHSV of 0.8 h$^{-1}$ showed stable performance with improved activity of more than 15° F. (FIG. 6), likely due to the lower amount of 900+° F. material (~25 wt. % in RAM vs. ~50 wt. % in GSC feed). Diluting the LC Finate product is one of the approaches to achieve the required performance.

ABQ1967 was prepared from ABQ1560 by distillation to a lower cutpoint and contained around 15 wt. % 900° F.+ material with an endpoint of around 930° F. This feed was tested with a base catalyst system (containing ICR 191) and compared to systems containing 34 and 44% of ICR 1000. A comparison of the base system with diluted ABQ1560 (612-37, FIG. 5) and non-diluted ABQ1967 (612-39, FIG. 9) showed similar activity and stable performance at LHSVs of 0.4 h$^{-1}$ and 0.8 h$^{-1}$, which suggests that reducing the 900+° F. content of the feed has similar effects on stability/activity of a catalyst system as dilution. A comparison of the base case with a 44% ICR 1000 case (FIG. 10) showed a decreased stability for the 44% ICR 1000 case with an activity advantage in the range of 10° F. We started a run with ABQ1967 over the 34% ICR 1000 containing catalyst system to check whether there is a heat management issue with 44% ICR 1000 as was observed with the ABQ1560 feed (see above).

The feed closest to Sincier design conditions was CGQ0107/CGQ0520, made from Neste LC Finate and SRC HVGO in a 50/50 blend. This feed was tested with 34% ICR 1000 and 44% ICR 1000 so far and is currently tested with a 55% ICR 250 system without ICR 1000. There is little difference between these two cases with the 44% ICR 1000 system having slightly lower activity in HDN. This may also be due to the fact that the 44% ICR 1000 system was first used for ABQ1560 conversion, which showed a high deactivation rate. For both cases the total sulfur and nitrogen content can be kept below 40 ppm S and below 30 ppm N in the 726-736° F. temperature range with values as low as 7 ppm N and 15 ppm S (see Table 3).

Figure 11:
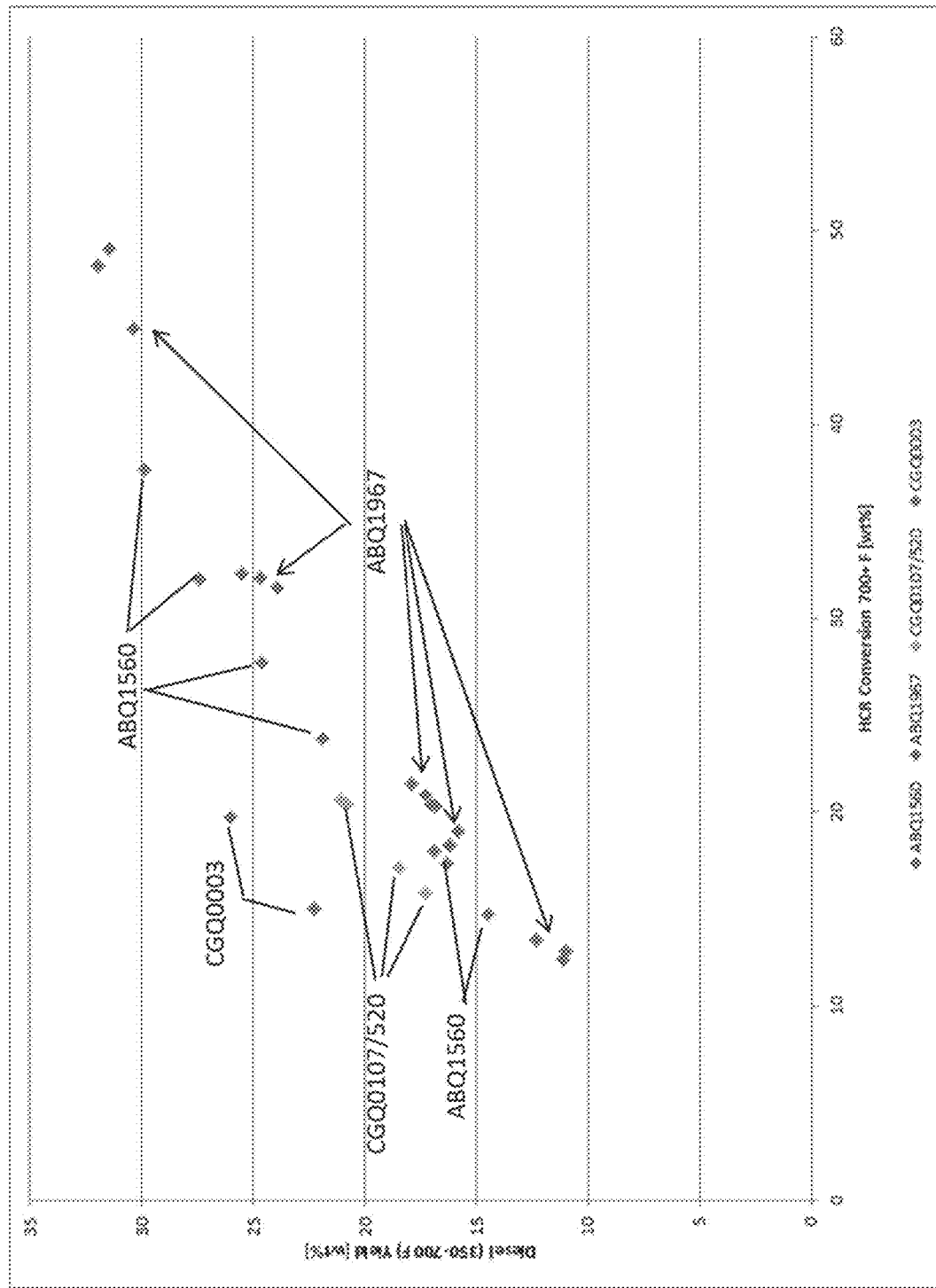
FIG. 11 graphically depicts normalized temperatures for hydrotreatment processes with an exemplary layered catalyst reactor system (two hydrocracking catalyst layers and two self-supported hydrotreating catalyst layers; BSU612-41).
Figure 12:
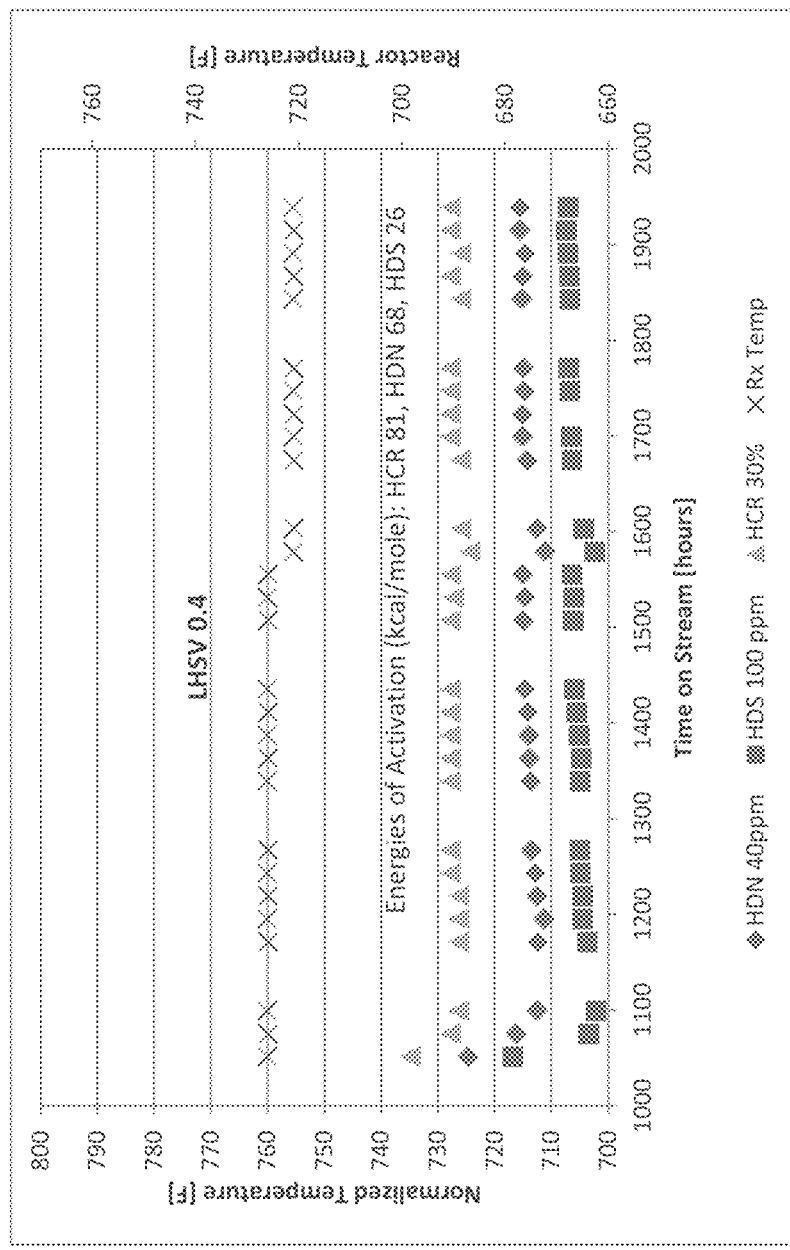
FIG. 12 graphically depicts normalized temperatures for hydrotreatment processes with an exemplary layered catalyst reactor system (two hydrocracking catalyst layers and two self-supported hydrotreating catalyst layers; BSU911-61).
Figure 13:
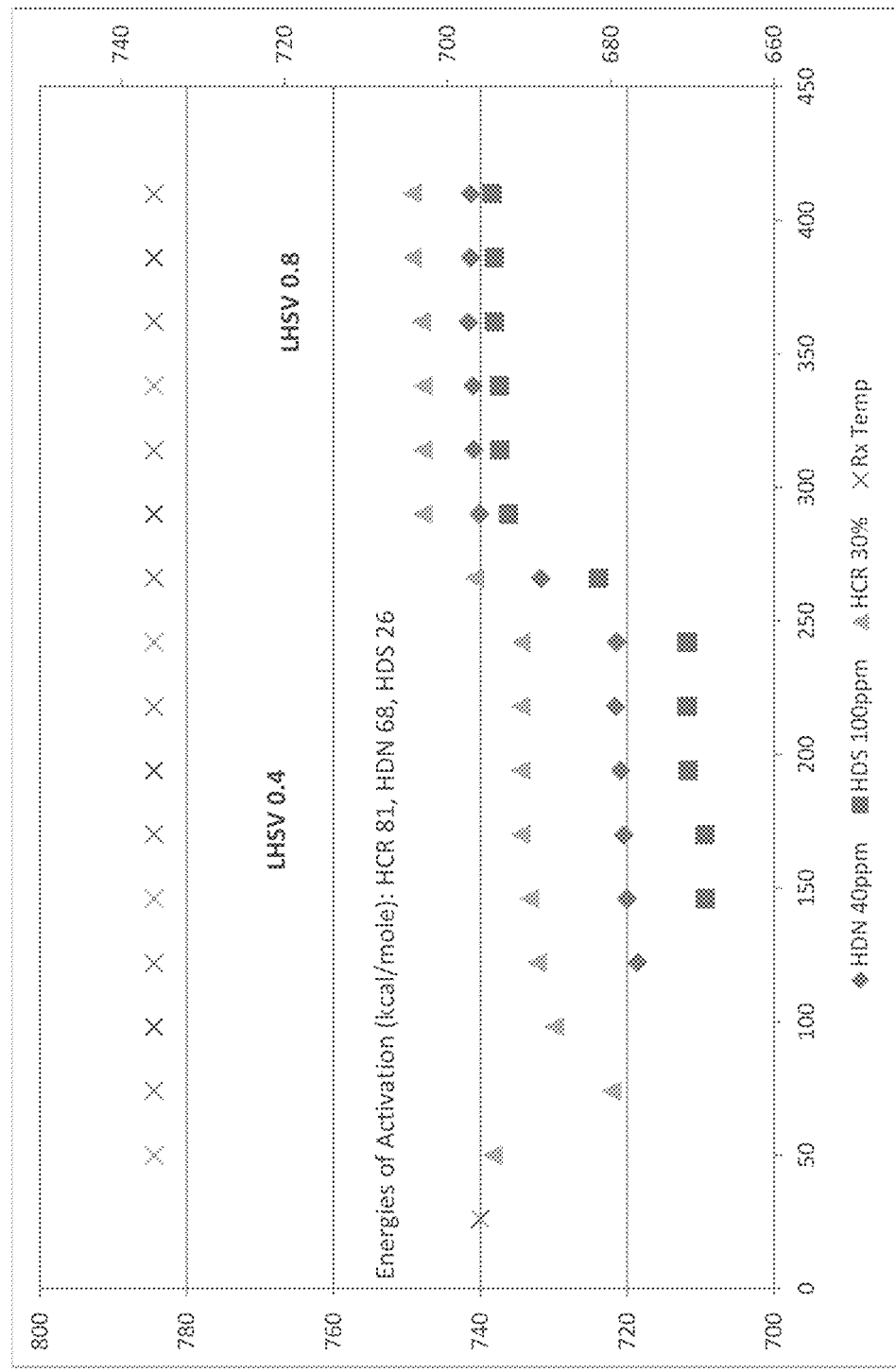
FIG. 13 graphically depicts Diesel Yield vs. Hydrocracking Conversion for Different Feeds.

Diesel Yield for all case varied between 13 and 32%, depending on conversion. FIG. 11 shows that diesel yield was depending on feed composition rather than catalyst system with the RAM based feed showing the highest yield at same conversion.

Observations

1. The stability of the catalyst system depends on cutpoint of the LC Finate as well as on dilution. Dilution to at least a 50/50 blend and decreasing end point and overall 900+° F. material improves the activity/stability of the system.

2. ICR 1000 addition enhances hydrodenitrogenation (HDN) and hydrodesulfurization (HDS) activity significantly but seems to show no improvement at higher ICR 1000 content as the comparison of 34 and 44% ICR 1000 cases show.

3. Without ICR 1000 low levels of nitrogen/sulfur (<10 ppm/30 ppm) cannot be achieved at required start-of-run temperature of around 730° F.

4. Diesel Yield (350-700° F. range) at same conversion depends on feed composition rather than catalyst system for the feeds and catalyst systems studied.

What is claimed is:

1. A layered catalyst reactor system comprising a vertical bed or stack of catalyst layers arranged from top to bottom in the following order:
   (i) a layer comprising one or more demetallization catalysts;
   (ii) a layer of one or more supported hydrotreating catalysts;
   (iii) a layer of one or more supported hydrocracking catalysts;
   (iv) a layer of one or more self-supported hydrotreating catalysts;
   (v) a layer of one or more supported hydrocracking catalysts;

(vi) a layer of one or more self-supported hydrotreating catalysts;
(vii) a layer of one or more supported hydrotreating catalysts;
wherein the total volume of the two layers comprising one or more self-supported hydrotreating catalysts is about 10 to about 50% of the total volume of catalysts in the vertical bed; and
wherein the total volume of the two layers comprising one or more supported hydrocracking catalysts is about 10 to about 30% of the total volume of catalysts in the vertical bed.

2. The layered catalyst reactor system of claim 1, wherein the one or more self-supported hydrotreating catalysts comprises about 5 to about 9 wt % molybdenum, about 21 to 31 wt % nickel, and about 33 to about 42 wt % tungsten.

3. The layered catalyst reactor system of claim 1, wherein the one or more demetallization catalysts are selected from the group consisting of: synthetic aluminum oxide or natural aluminum silicate enriched with the oxides of molybdenum, cobalt and nickel.

4. The layered catalyst reactor system of claim 1, wherein the one or more supported hydrotreating catalysts are selected from the group consisting of: catalysts comprising at least one Group VIII metal and at least one Group VIB metal on a support material selected from the group consisting of alumina, zeolites, amorphous silica-alumina, and titania-alumina.

5. The layered catalyst reactor system of claim 1, wherein the one or more supported hydrotreating catalysts are selected from the group consisting of: catalysts comprising Pd or Pt.

6. The layered catalyst reactor system of claim 1, wherein the one or more hydrocracking catalysts are selected from the group consisting of: catalysts comprising nickel, nickel-cobalt-molybdenum, cobalt-molybdenum and nickel-tungsten and/or nickel-molybdenum.

7. The layered catalyst reactor system of claim 1, wherein the one or more hydrocracking catalysts comprise porous support materials comprising a refractory oxide material.

8. The layered catalyst reactor system of claim 1, wherein the one or more hydrocracking catalysts comprise nickel, cobalt, molybdenum and/or tungsten.

9. A layered catalyst reactor system comprising a vertical bed or stack of catalyst layers arranged from top to bottom in the following order:
(i) a layer comprising one or more demetallization catalysts;
(ii) a layer of one or more supported hydrotreating catalysts;
(iii) a layer of one or more supported hydrocracking catalysts;
(iv) a layer of one or more self-supported hydrotreating catalysts;
(v) a layer of one or more supported hydrocracking catalysts;
(vi) a layer of one or more self-supported hydrotreating catalysts;
(vii) a layer of one or more supported hydrocracking catalysts;
(viii) a layer of one or more self-supported hydrotreating catalysts;
(ix) a layer of one or more supported hydrotreating catalysts;
wherein the total volume of the three layers comprising one or more self-supported hydrotreating catalysts is about 9 to about 45% of the total volume of catalysts in the vertical bed; and
wherein the total volume of the three layers comprising one or more supported hydrocracking catalysts is about 15 to about 30% of the total volume of catalysts in the vertical bed.

10. The layered catalyst reactor system of claim 9, wherein the one or more self-supported hydrotreating catalysts comprises about 5 to about 9 wt % molybdenum, about 21 to 31 wt % nickel, and about 33 to about 42 wt % tungsten.

11. The layered catalyst reactor system of claim 9, wherein the one or more demetallization catalysts are selected from the group consisting of: synthetic aluminum oxide or natural aluminum silicate enriched with the oxides of molybdenum, cobalt and nickel.

12. The layered catalyst reactor system of claim 9, wherein the one or more supported hydrotreating catalysts are selected from the group consisting of: catalysts comprising at least one Group VIII metal and at least one Group VIB metal on a support material selected from the group consisting of alumina, zeolites, amorphous silica-alumina, and titania-alumina.

13. The layered catalyst reactor system of claim 9, wherein the one or more supported hydrotreating catalysts are selected from the group consisting of: catalysts comprising Pd or Pt.

14. The layered catalyst reactor system of claim 9, wherein the one or more hydrocracking catalysts are selected from the group consisting of: catalysts comprising nickel, nickel-cobalt-molybdenum, cobalt-molybdenum and nickel-tungsten and/or nickel-molybdenum.

15. The layered catalyst reactor system of claim 9, wherein the one or more hydrocracking catalysts comprise porous support materials comprising a refractory oxide material.

16. The layered catalyst reactor system of claim 9, wherein the one or more hydrocracking catalysts comprise nickel, cobalt, molybdenum and/or tungsten.

17. A process for hydrotreatment of hydrocarbon feedstocks comprising: (i) contacting a hydrocarbon feedstock which contains contaminants comprised of metals, sulfur, nitrogen and olefins with a layered catalyst reactor system in the presence of hydrogen to produce hydrocarbon product having a lower content of metals sulfur, nitrogen and olefins than the hydrocarbon feedstock; (ii) passing the hydrocarbon feedstock sequentially through the layers of the layered catalyst reactor system vertically from top to bottom; and (iii) recovering the hydrocarbon product from the bottom of the layered catalyst reactor system;
wherein the layered catalyst system comprises a vertical bed or stack of catalyst layers arranged from top to bottom in the following order:
(i) a layer comprising one or more demetallization catalysts;
(ii) a layer of one or more supported hydrotreating catalysts;
(iii) a layer of one or more supported hydrocracking catalysts;
(iv) a layer of one or more self-supported hydrotreating catalysts;
(v) a layer of one or more supported hydrocracking catalysts;
(vi) a layer of one or more self-supported hydrotreating catalysts;

(vii) a layer of one or more supported hydrotreating catalysts;

wherein the total volume of the two layers comprising one or more self-supported hydrotreating catalysts is about 10 to about 50% of the total volume of catalysts in the vertical bed; and wherein the total volume of the two layers comprising one or more supported hydrocracking catalysts is about 10 to about 30% of the total volume of catalysts in the vertical bed;

or wherein the layered catalyst reactor system comprises a vertical bed or stack of catalyst layers arranged from top to bottom in the following order:

(i) a layer comprising one or more demetallization catalysts;

(ii) a layer of one or more supported hydrotreating catalysts;

(iii) a layer of one or more supported hydrocracking catalysts;

(iv) a layer of one or more self-supported hydrotreating catalysts;

(v) a layer of one or more supported hydrocracking catalysts;

(vi) a layer of one or more self-supported hydrotreating catalysts;

(vii) a layer of one or more supported hydrocracking catalysts;

(viii) a layer of one or more self-supported hydrotreating catalysts;

(ix) a layer of one or more supported hydrotreating catalysts;

wherein the total volume of the three layers comprising one or more self-supported hydrotreating catalysts is about 9 to about 45% of the total volume of catalysts in the vertical bed; and wherein the total volume of the three layers comprising one or more supported hydrocracking catalysts is about 15 to about 30% of the total volume of catalysts in the vertical bed.

18. The process of claim 17, wherein the operating temperature of layered catalyst reactor system is in the range of about 700 to about 775° F.

19. The process of claim 17, wherein the weight hourly space velocity (WHSV) of the process is in the range of about 0.4 to about 1.1 hr-1.

20. The process of claim 17, wherein the liquid hourly space velocity (LHSV) of the process is in the range of about 0.3 to about 0.9 hr-1.

21. The process of claim 17, wherein the normalized temperature of the layered catalyst reactor system remains less than about 770° F. during the process.

* * * * *